US008703161B2

(12) United States Patent
Maes et al.

(10) Patent No.: US 8,703,161 B2
(45) Date of Patent: *Apr. 22, 2014

(54) **SKIN REPAIR COMPOSITIONS COMPRISING CIRCADIAN GENE ACTIVATORS AND A SYNERGISTIC COMBINATION OF *SIRT*1 GENE ACTIVATORS**

(75) Inventors: Daniel H. Maes, Huntington, NY (US); Nadine A. Pernodet, Huntington, NY (US); Thomas Mammone, Farmingdale, NY (US); Edward Pelle, Valley Stream, NY (US); Donald F. Collins, Plainview, NY (US); Lenny Slutsky, Hauppauge, NY (US); Kerri Goldgraben, Commack, NY (US)

(73) Assignee: ELC Management, LLC, New York, NY (US)

( * ) Notice: Subject to any disclaimer, the term of this patent is extended or adjusted under 35 U.S.C. 154(b) by 879 days.

This patent is subject to a terminal disclaimer.

(21) Appl. No.: 12/489,619

(22) Filed: Jun. 23, 2009

(65) Prior Publication Data

US 2010/0028317 A1 Feb. 4, 2010

Related U.S. Application Data

(63) Continuation-in-part of application No. 11/837,658, filed on Aug. 13, 2007, and a continuation-in-part of application No. 12/367,705, filed on Feb. 9, 2009.

(51) Int. Cl.
*A61K 8/37* (2006.01)
*A61K 8/55* (2006.01)

(52) U.S. Cl.
USPC ............ 424/401; 424/94.1; 514/1.1; 514/764

(58) Field of Classification Search
None
See application file for complete search history.

(56) References Cited

U.S. PATENT DOCUMENTS

| | | | |
|---|---|---|---|
| 3,215,724 A | 11/1965 | Strobel et al. | |
| 3,439,088 A | 4/1969 | Edman | |
| 3,781,417 A | 12/1973 | Welters et al. | |
| 3,818,105 A | 6/1974 | Coopersmith et al. | |
| 4,003,966 A | 1/1977 | Napier et al. | |
| 4,677,152 A | 6/1987 | Allen et al. | |
| 5,077,211 A | 12/1991 | Yarosh | |
| 5,190,762 A | 3/1993 | Yarosh | |
| 5,272,079 A | 12/1993 | Yarosh | |
| 5,296,231 A | 3/1994 | Yarosh | |
| 5,302,389 A | 4/1994 | Kripke et al. | |
| 6,270,780 B1 | 8/2001 | Carson et al. | |
| 6,414,037 B1 | 7/2002 | Pezzuto et al. | |
| 6,572,882 B1 | 6/2003 | Vercauteren et al. | |
| 6,730,308 B1 | 5/2004 | Sefton | |
| 7,758,878 B2 | 7/2010 | Scimeca et al. | |
| 7,842,670 B2 * | 11/2010 | Dal Farra et al. | 514/18.8 |
| 8,193,155 B2 * | 6/2012 | Maes et al. | 514/21.9 |
| 2002/0086042 A1 | 7/2002 | Delrieu et al. | |
| 2002/0173472 A1 | 11/2002 | Pezzuto et al. | |
| 2003/0223982 A1 | 12/2003 | Schlotmann et al. | |
| 2004/0057917 A1 | 3/2004 | Wolf et al. | |
| 2004/0142007 A1 | 7/2004 | Moussou et al. | |
| 2004/0161408 A1 | 8/2004 | Lee et al. | |
| 2006/0002884 A1 | 1/2006 | Golz-Berner et al. | |
| 2006/0165641 A1 * | 7/2006 | Pillai et al. | 424/70.22 |
| 2006/0257386 A1 | 11/2006 | Zimmerman et al. | |
| 2006/0257509 A1 | 11/2006 | Zimmerman et al. | |
| 2006/0269616 A1 | 11/2006 | Giampapa | |
| 2007/0110686 A1 * | 5/2007 | Lowe et al. | 424/59 |
| 2007/0243148 A1 | 10/2007 | Andre et al. | |
| 2007/0254021 A1 | 11/2007 | Scimeca et al. | |
| 2008/0095866 A1 | 4/2008 | Declercq et al. | |
| 2008/0107613 A1 | 5/2008 | Hultsch et al. | |
| 2008/0274456 A1 | 11/2008 | Yankner et al. | |
| 2009/0028895 A1 | 1/2009 | Smith | |
| 2009/0035243 A1 | 2/2009 | Czarnota et al. | |
| 2009/0047309 A1 | 2/2009 | Maes et al. | |
| 2009/0082278 A1 | 3/2009 | Dal Farra et al. | |
| 2009/0220481 A1 | 9/2009 | Maes et al. | |

(Continued)

FOREIGN PATENT DOCUMENTS

DE 202004012807 11/2004
EP 1634576 3/2006

(Continued)

OTHER PUBLICATIONS

Kawara, Shigeru, et al.; Low-dose Ultraviolet B Rays Alter the mRNA Expression of the Circadian Clock Genes in Cultured Human Keratinocytes; The Journal of Investigative Dermatology; vol. 119, No. 6; pp. 1220-1223; Dec. 2002.

Sosniyenko, Serhiy, et al.; Influence of photoperiod duration and light-dark transitions on entrainment of Per1 and Per 2 gene and protein expression in subdivisions of the mouse suprachiasmatic nucleus; The European Journal of Neuroscience; vol. 30, No. 9; pp. 1802-1814; Nov. 2009; Blackwell Science, Paris.

(Continued)

*Primary Examiner* — Karlheinz R Skowronek
*Assistant Examiner* — Roy Teller
(74) *Attorney, Agent, or Firm* — Peter Giancang

(57) ABSTRACT

Compositions and methods for enhancing repair of damaged DNA in skin cells. Topical compositions comprising at least one agent that upregulates circadian gene expression in skin cells and at least one non-circadian agent that delays mitosis in skin cells. Preferably, such compositions comprise one or more keratinocyte clock and per1 gene activators, along with SIRT1 or one or more sirt1 activators. More preferably, the sirt1 activator is a synergistic combination of specific peptidic sirt1 activators and resveratrol. Preferably, such compositions are easy to use, efficacious, cosmetically acceptable, chemically, thermodynamically and light stable, safe for topical use, have little or no side effects, and commercially feasible in a personal care marketplace.

13 Claims, 3 Drawing Sheets

(56) References Cited

U.S. PATENT DOCUMENTS

| | | |
|---|---|---|
| 2010/0028317 A1 | 2/2010 | Maes et al. |
| 2010/0080845 A1 | 4/2010 | Maes et al. |
| 2011/0250251 A1 | 10/2011 | Maes et al. |

FOREIGN PATENT DOCUMENTS

| | | |
|---|---|---|
| EP | 1 642 560 | 4/2006 |
| JP | 2002-326905 | 11/2002 |
| JP | 2004-532790 | 10/2004 |
| JP | 2005-532375 | 10/2005 |
| KR | 10-2007-0079933 | 8/2007 |
| RU | 2128504 | 4/1999 |
| WO | WO99/57137 | 11/1999 |
| WO | WO01/91695 | 12/2001 |
| WO | WO03/025151 | 3/2003 |
| WO | WO2005/034891 | 4/2005 |
| WO | WO2006/029484 | 3/2006 |
| WO | WO2007/104867 | 9/2007 |

OTHER PUBLICATIONS

Sporl, Florian, et al.; A Circadian Clock in HaCaT Keratinocytes; The Journal of Investigative Dermatology; vol. 131, No. 2; pp. 338-348; Feb. 2011.

Krutmann, et al.; Modern Photoprotection of Human Skin; Skin Aging; Gilchrest, B.A.; Krutmann, J.; Ed. Springer-Verlag; Berlin Heidelberg; Ch. 9; pp. 103-112; 2006.

PCT International Search Report; International Application No. PCT/US2008/071061; Completion Date: Jan. 29, 2009; Date of Mailing: Jan. 29, 2009.

PCT Written Opinion of the International Searching Authority, or the Declaration; International Application No. PCT/US2008/071061; Completion Date: Jan. 29, 2009; Mailing Date: Jan. 29, 2009.

PCT International Search Report; International Application No. PCT/US20101023435; Completion Date: Dec. 10, 2010; Date of Mailing: Dec. 10, 2010.

PCT Written Opinion of the International Searching Authority, or the Declaration; International Application No. PCT/US2010/023435; Completion Date: Dec. 10, 2010; Mailing Date: Dec. 10, 2010.

Barnet; Barnet Products Corporation; Roxisomes-preliminary report; DNA Protection from Oxygen Radicals; www.barnetproducts.com.

Collis, et al.; Emerging links between the biological clock and the the DNA damage response; Chromosoma; 116; pp. 331-339; 2007.

Gery, et al.; The Circadian Gene Peri Plays and Important Role in Cell Growth and DNA Damage Control in Human Cancer Cells; Molecular Cell; 22; pp. 375-382; May 2006.

Fishel, et al.; The DNA base excision repair protein Apel/Ref-1 as a therapeutic and chemopreventive target; Molecular Aspects of Medicine; vol. 28; pp. 375-395; May 2007.

Yarosh, et al.; After sun reversal of DNA damage: enhancing skin repair; Mutation Research; vol. 571; No. 1-2; pp. 57-64; Apr. 2005.

PCT International Search Report; International Application No. PCT/US10/037871; Completion Date: Dec. 31, 2010; Date of Mailing: Jan. 3, 2011.

PCT Written Opinion of the International Searching Authority, or The Declaration; International Application No. PCT/ US10/037871; Completion Date: Dec. 31, 2010; Date of Mailing: Jan. 3, 2011.

Supplementary European Search Report; EP08782328.2; Completion Date: Feb. 23, 2011; Date of Mailing: Mar. 1, 2011.

Yamaguchi, et al.; Melanin mediated apoptosis of epidermal cells damaged by ultraviolet radiation: factors influencing the incidence of skin cancer; Arch. Dermatol. Res.; 300 (Suppl 1):S43-S50; 2008.

Reddy, et al.; Circadian clocks: neural and peripheral pacemakers that impact upon the cell division cycle.; Mutation Research; 574 (1-2):76-91; http://www.ncbi.nlm.nih.gov/pubmed/15914209?dopt=Abstract; Epub Apr. 15, 2005; Jul. 2005.

Vallone, et al.; Start the Clock! Circadian Rhythms and Development; Developmental Dynamics; 236; pp. 142-155; 2007.

Chua, et al.; Mammalian SIRT1 limits replicative life span in response to chronic genotoxic stress; Cell Metabolism; vol. 2; pp. 67-76; Jul. 2005.

Langley, et al.; Human SIR2 deacetylates p53 and antagonizes PML/p53-induced cellular senescence; The EMBO Journal; vol. 21; No. 10; pp. 2383-2396; 2002.

Kuningas, et al.; SIRT1 Gene, Age-Related Diseases, and Mortality: The Leiden 85-Plus Study; The Journals of Gerontology Series A: Biological Sciences and Medical Sciences; 62:960-965; http://biomed.gerontologyjounrals.org/cgi;content/abstract/62/9/960; 2007.

Bjarnason, et al.; Circadian variation of cell proliferation and cell cycle protein expression in man: clinical implications.; Prog Cell Cycle Res.; 4:193-206; http://www.ncbi.nlm.nih.gov/pubmed/10740826?dopt=Abstract; 2000.

Agar, et al.; Melanogenesis: a photoprotective response to DNA damage?; Mutation Research; 571 (1-2):121-32; http://www.ncbi.nlm.nih.gov/pubmed/15748643; Epub Jan. 23, 2005; Apr. 2005.

Dickmeis, Thomas; Glucocorticoids and the circadian clock; Review; Journal of Endocrinology; Circadian rhythms and glucocorticoids; 200; pp. 3-22; www.endocrinology-journals.org; 2009.

Nagoshi, et al.; Circadian Gene Expression in Individual Fibroblasts: Cell-Autonomous and Self-Sustained Oscillators Pass Time to Daughter Cells; Cell; vol. 119; pp. 693-705; Nov. 2004.

Dryden, et al.; Role for Human SIRT2 NAD-Dependent Deacetylase Activity in Control of Mitotic Exit in the Cell Cycle; Molecular and Cellular Biology; vol. 23; No. 9; pp. 3173-3185; May 2003.

Zanello, et al.; Expression of the Circadian Clock Genes clock and period 1 in Human Skin; The Journal of Investigative Dermatology; Circadian Gene Expression in Skin; vol. 115; No. 4; Oct. 2000.

Ünsal-Kaçmaz; Coupling of Human Circadian and Cell Cycles by the Timeless Protein; Molecular and Cellular Biology; vol. 25; No. 8; pp. 3109-3116; Apr. 2005.

Clayton, et al.; Keeping time with the human genome; Analysis; Nature; Dept. of Genetics, University of Leicester, Leicester UK; vol. 409; pp. 829-831; www.nature.com; Feb. 2001.

Hunt, et al.; Riding Tandem: Circadian Clocks and the Cell Cycle; Leading Edge; Minireview; Cell; 129; pp. 461-464; May 2007.

Asher et al., SIRT1 Reguates Circadian Clock Gene Expression through PER2 Deacetylation: Cell 134, 317-328, Jul. 25, 2008.

Supplemental European Search Report; EP10739214.4; Completion Date: Sep. 18, 2012; Date of Mailing: Sep. 25, 2012.

\* cited by examiner

SEQUENCE LISTING

```
<160> NUMBER OF SEQ ID NOS: 8

<210> SEQ ID NO 1
<211> LENGTH: 13
<212> TYPE: PRT
<213> ORGANISM: Artificial Sequence
<220> FEATURE:
<223> OTHER INFORMATION: CLOCK and/or PER1 gene activator
<220> FEATURE:
<221> NAME/KEY: misc_feature
<222> LOCATION: (1)..(4)
<223> OTHER INFORMATION: Xaa can be any naturally occurring amino acid
      or no amino acid
<220> FEATURE:
<221> NAME/KEY: misc_feature
<222> LOCATION: (5)
<223> OTHER INFORMATION: Xaa can be threonine or serine or no amino
      acid
<220> FEATURE:
<221> NAME/KEY: misc_feature
<222> LOCATION: (9)
<223> OTHER INFORMATION: Xaa can be isoleucine, leucine, proline,
      valine, alanine, glycine or no amino acid
<220> FEATURE:
<221> NAME/KEY: misc_feature
<222> LOCATION: (10)..(13)
<223> OTHER INFORMATION: Xaa can be any naturally occurring amino acid
      or no amino acid

<400> SEQUENCE: 1

Xaa Xaa Xaa Xaa Xaa Ser Thr Pro Xaa Xaa Xaa Xaa Xaa
1               5                   10

<210> SEQ ID NO 2
<211> LENGTH: 7
<212> TYPE: PRT
<213> ORGANISM: Artificial Sequence
<220> FEATURE:
<223> OTHER INFORMATION: CLOCK and/or PER1 gene activator

<400> SEQUENCE: 2

Tyr Val Ser Thr Pro Tyr Asn
1               5
```

```
<210> SEQ ID NO 3
<211> LENGTH: 5
<212> TYPE: PRT
<213> ORGANISM: Artificial Sequence
<220> FEATURE:
<223> OTHER INFORMATION: CLOCK and/or PER1 gene activator

<400> SEQUENCE: 3

Val Ser Thr Pro Glu
1               5

<210> SEQ ID NO 4
<211> LENGTH: 6
<212> TYPE: PRT
<213> ORGANISM: Artificial Sequence
<220> FEATURE:
<223> OTHER INFORMATION: CLOCK and/or PER1 gene activator

<400> SEQUENCE: 4

Leu His Ser Thr Pro Pro
1               5

<210> SEQ ID NO 5
<211> LENGTH: 6
<212> TYPE: PRT
<213> ORGANISM: Artificial Sequence
<220> FEATURE:
<223> OTHER INFORMATION: CLOCK and/or PER1 gene activator

<400> SEQUENCE: 5

Arg His Ser Thr Pro Glu
1               5

<210> SEQ ID NO 6
<211> LENGTH: 5
<212> TYPE: PRT
<213> ORGANISM: Artificial Sequence
<220> FEATURE:
<223> OTHER INFORMATION: CLOCK and/or PER1 gene activator

<400> SEQUENCE: 6

His Ser Thr Pro Glu
1               5

<210> SEQ ID NO 7
<211> LENGTH: 13
<212> TYPE: PRT
<213> ORGANISM: Artificial Sequence
<220> FEATURE:
<223> OTHER INFORMATION: SIRT1 gene activator
<220> FEATURE:
<221> NAME/KEY: misc_feature
<222> LOCATION: (1)..(3)
<223> OTHER INFORMATION: Xaa can be any naturally occurring amino acid
      or no amino acid
<220> FEATURE:
<221> NAME/KEY: misc_feature
<222> LOCATION: (11)..(13)
<223> OTHER INFORMATION: Xaa can be any naturally occurring amino acid
      or no amino acid

<400> SEQUENCE: 7

Xaa Xaa Xaa Gly Leu Tyr Asp Asn Leu Glu Xaa Xaa Xaa
1               5                   10

<210> SEQ ID NO 8
<211> LENGTH: 7
<212> TYPE: PRT
<213> ORGANISM: Artificial Sequence
<220> FEATURE:
```

```
<223> OTHER INFORMATION: SIRT1 gene activator

<400> SEQUENCE: 8

Gly Leu Tyr Asp Asn Leu Glu
1               5
```

SKIN REPAIR COMPOSITIONS COMPRISING CIRCADIAN GENE ACTIVATORS AND A SYNERGISTIC COMBINATION OF *SIRT*1 GENE ACTIVATORS

The present application is a continuation in part of pending application U.S. Ser. No. 11/837,658, filed Aug. 13, 2007, and a continuation in part of pending application U.S. Ser. No. 12/367,705, filed Feb. 9, 2009, both herein incorporated by reference, in their entirety.

TECHNICAL FIELD

The invention is in the field skin treatment. More particularly, the invention pertains to compositions and methods for enhancing repair of damaged DNA in skin cells.

BACKGROUND OF THE INVENTION

It is now well appreciated that the skin is under daily assault from various environmental and lifestyle factors. A short list of these factors includes UVA radiation, UVB radiation, pollution, cigarette smoke, poor diet, insufficient rest, and psychological stress. This assault manifests as damage to skin cell DNA and proteins. Lines and wrinkles in the skin are among the less serious outcomes of skin cell damage, while melanoma is one of the more serious.

DNA Damage

Some environmental and lifestyle factors interact directly with skin cell DNA and/or proteins to cause damage, some factors cause damage indirectly, and some factors may do both. An example of direct DNA damage would be when skin cell DNA absorbs photons from the UVB part of the spectrum. The absorption of photons may cause mutations in the DNA sequence. For example, about 8% of all melanoma occurrence is due to direct DNA mutation.

An example of indirect damage to skin cell DNA and proteins is seen when ultraviolet photons enter the skin and are absorbed by chromophores. In an excited state, chromophores enter into reactions that lead to the formation of reactive oxygen species. For example, in human skin, UVB exposure is associated with the production of hydrogen peroxide, while UVA is associated with production of singlet oxygen. If the skin is unable to maintain homeostasis by neutralizing the reactive species, then the reactive species will damage skin cell DNA and proteins, through oxidation. This damage to DNA and proteins is called oxidative stress and is a major cause of skin aging. Also, about 92% of all melanoma occurrence is due to indirect, oxidative DNA damage.

DNA Damage: Prevention and Containment Verses Repair

DNA containing skin cells include keratinocyte stem cells and melanocytes. It is estimated that a single sun burn results in hundreds of thousands of DNA mutagenic base modifications such as T-T (thiamine-thiamine) dimers; 8-oxo-7,8-dihydro-2'-deoxyguanosine (8-oxo-DG); O6MeG (06-methyl guanine); cyclobutane pyrimidine dimers (CPD); and 6-4 photoproducts (6-4PP) in affected cells. These mutations trigger various responses within the skin cells, which may lead to prevention of further DNA damage or apoptosis of the cell. For example, melanin production in melanocytes is known to be upregulated by UV radiation, as a protective measure. To deal with the threat from UV, melanin is produced by melanocytes in the lower epidermis, and with the help of outwardly migrating keratinocytes, is distributed throughout the upper and lower epidermis. In the first instance melanin seems to prevent further UV-induced DNA damage by acting as a UV filter that limits the amount of UV that penetrates to the lower epidermis, where melanocytes and keratinocyte stem cells are located. However, as a second line of defense, melanin contains DNA damage due to UV radiation by inducing apoptosis of keratinocytes. By promoting apoptosis, damaged DNA is contained, having less chance of being passed on to daughter cells (see, for example, Yamaguchi et al., Melanin mediated apoptosis of epidermal cells damaged by ultraviolet radiation: factors influencing the incidence of skin cancer; *Arch Dermatol Res.* 2008 April; 300 Suppl 1: S43-S50).

Apart from preventing and containing DNA damage, healthy keratinocytes and melanocytes have a natural internal mechanism for repairing DNA lesions. These mechanisms are different than those of prevention and containment, which involve different (although sometimes overlapping) reaction cascades. Compositions and methods of the present invention are foremost concerned with repair of DNA damage.

Cellular repair mechanisms exist to repair DNA lesions from various causes, not just the UV-induced damage that we have been discussing. However, repair of DNA lesions takes time. For example, repair of TT dimers and 6-4PP damage formed by UVB exposure may take up to 48 and 8 hours respectively, if not accelerated by an exogenous influence. Repair of 8-oxo-dG and 06MeG lesions due to UVA or UVB exposure, ozone, or smoke and pollution may take up to 2 hours. Ideally, DNA lesions are repaired before cell division occurs. If not, the preferred outcome is apoptosis. But if the DNA damage happens to adversely affect the upregulation of apoptosis, or if the mutation goes undetected, then the damaged DNA may be passed on to the next generation. Compositions and methods of the present invention are foremost concerned with maximizing the repair of DNA damage before cell division occurs.

A Cell's Preventative and Repair Mechanisms are Controlled by a Circadian Clock

Under normal conditions, cellular functions, including DNA expression and repair, do not occur at random times with equal probability. Rather, each cell has an endogenous cycle (or clock) of about 24 hours (i.e. a circadian rhythm), and the activities of the cell are regulated by this endogenous cycle. Absent some external stimulus, each cell would free-run according to its endogenous clock. However, the endogenous clocks of cells throughout the body are synchronized. In order to synchronize the activities of cells with each other and with the environment, the body is able to accept cues from the environment. The most notable environmental cue is the presence of absence of daylight. Thus, the circadian cycle consists of light and dark phases that roughly coincide with the phases of the solar day.

It is now appreciated that circadian rhythms allow cells to anticipate changes in the environment that might affect the cells, and to adapt to those changes in a timely fashion. As long as the genetic machinery of cellular circadian rhythms are functioning properly, cells carry out each of their many functions in a synchronized manner, at a time that is optimal for cell viability and/or homeostasis. For example, as daylight approaches (but even before the skin is under assault from UV), certain genes are activated to produce proteins that protect the cells against anticipated UV radiation damage. Then, as daylight wanes, these genes are turned off. On the other hand, the circadian genes themselves may be subject to attack by environmental factors. Damage to one or more genes that regulate a cell's circadian rhythm can put a cell out of sync with the environment and with other cells.

The Core Circadian Mechanism

Transcription factors are proteins that bind to specific DNA sequences to control the transfer of genetic information from DNA to RNA. The core circadian mechanism, or "cell clock", is comprised of transcription factors that participate in out-of-phase, negative and positive feedback loops, that lead to oscillating gene transcription.

In the main negative feedback loop of mammals, a heterodimer of CLOCK and BMAL1 transcription factors activates transcription of the period (per) and cryptochrome (cry) genes. In humans, the period gene is actually a family of three genes per1, per2, and per3 and the cry gene family includes of cry1 and cry2. Following their translation, the PER and CRY proteins migrate into the cytoplasm and form PER/CRY complexes. Posttranslational regulation creates an intentional delay after which the PER/CRY complexes relocate into the cell nucleus. The concentrations of PER and CRY in the nucleus peak at the end of circadian daytime, at which time the CRY proteins then act to inhibit transcriptional activity of the CLOCK/BMAL1 heterodimer. Thus, CRY seems to turn off its own transcription.

On the other hand, in one positive feedback loop, PER2 upon translocating to the nucleus, seems to upregulate the transcription of BMAL1, eventually leading to the transcription of period and cry genes. Also, the CLOCK/BMAL1 dimer seems to upregulate rev-erbα and rora genes. Rora activates BMAL1 transcription, while rev-erbα suppresses CLOCK and BMAL1. The peak activities of the so called "canonical clock genes" (clock, bmal1, per1, per2, per3, cry1 and cry2) are out of phase, such that a self-sustaining loop results, having a period of approximately 24 hours.

The Cell Cycle

The cell cycle refers to the series of events that takes place in a cell leading to division and replication of the cell. The cycle is usually described as four or five sequential phases requiring about 24 hours to complete. Within each phase of the cell cycle, there are checkpoints that ensure that all requisite processes of a given phase are completed prior to initiation of the next phase. In human cells, the "first" phase is the Synthesis (S) phase in which the DNA of a cell is copied and synthesized. The S phase may typically last from 6-8 hours. In the G2 phase, lasting 3-4 hours, proteins are synthesized and the cell doubles in size. During Mitosis (M), the nuclear envelope breaks down so that each copy of the genetic material can separate to opposite poles of the cell. Following the formation of a new nuclear envelope around each set of chromosomes, the cell is pinched in two (cytokinesis). The M phase is about 1 hour long. The fourth and longest phase (6-12 hours) is G1 which is characterized by RNA and protein synthesis. From the G1 phase, a cell may again enter the S phase or it may enter the G0 phase. In G0, the cell is quiescent. G0 may last for days or years. Stem cells may return from the G0 phase, entering at G1. Differentiated cells do not generally return from G0. Also, cells with damaged DNA may enter G0, rather than apoptosis.

Cell Cycle Checkpoints Inhibit Damaged DNA from Being Passed On

During cell division, checkpoints are used to regulate the progress of the cell through the cell cycle. Checkpoints prevent a cell from progressing to the next phase until completion of all necessary processes, including any repair of damaged DNA. In this way, checkpoints ensure that damaged or incomplete DNA is not passed on to daughter cells. Several checkpoints exist. The G1/S checkpoint (the Restriction checkpoint) interrupts the cell cycle so that the "decision" can be made to enter the quiescent phase or not. At the G2/M checkpoint the cell cycle is halted if damaged DNA is detected, which is not unusual. The Postreplication checkpoint concerns damaged DNA that has been replicated in the Synthesis phase. The replication of damaged DNA triggers a cellular response that prevents cell cycle progression until postreplication repair processes are completed. In human cells, the postreplication checkpoint makes time for repair by delaying the onset of the Mitosis phase. The chk1 gene exerts control over the postreplication checkpoint, while the p53 gene plays an important role in triggering the control mechanisms at both G1/S and G2/M checkpoints.

The Circadian Clock Also Regulates Cell Proliferation

In recent years, the importance of circadian clock in regulating cell proliferation has been appreciated. For example:

"Disruption of circadian timing . . . has far reaching consequences for normal regulation of cell division." (Reddy et al., 2005 Circadian clocks: neural and peripheral pacemakers that impact upon the cell division cycle. *Mutation Research* 574 76-91).

"Detailed insight into the mechanisms whereby clock components interact with the cell cycle regulatory machinery has come from recent mouse studies. For example, . . . the delay between removal of liver tissue (partial hepatectomy) and the subsequent first wave of mitosis depends upon the time of day that the surgery was performed." (Vallone et al., 2007 Start the clock! Circadian rhythms and development. *Developmental Dynamics* 236 142-155).

"From cyanobacteria to higher vertebrates, there are many examples of the circadian clock "gating" S-phase and mitosis of the cell cycle to occur during the night period." (Vallone et al.). [Presumably, DNA synthesis and mitosis occur at night to protect DNA from harmful UV or other ionizing radiation from the sun.]

Thus, the circadian clock exerts an overarching influence on the cellular cycle of DNA and protein synthesis, mitosis and cytokinesis, RNA synthesis and repair. Therefore, when environmental factors interfere with a cell's circadian mechanism, cellular function is compromised. We postulate that when treatment can entrain or resynchronize a cell's circadian clock, or when treatment can restore "normal" levels of circadian gene expression, then cellular functioning may be improved, cell damage may be repaired in an accelerated fashion, or apoptosis may occur in a more timely fashion.

The Environment can Put the Circadian Rhythm Out of Sync

Agents that interfere with one or more genes that regulate a cell's circadian rhythm can put a cell out of sync with the environment and with other cells. For example, in the hours following UV exposure, perhaps as many as 20 hours, the levels of clock, bmal1 and per1 gene expression in human keratinocytes are significantly depressed (see FIG. 1). By "significantly depressed" we mean below the minimum expression that these genes experience in their normal circadian cycle, as described above. Furthermore, following UV exposure, the usual pattern of gene expression, which may be described as roughly sinusoidal, is lost.

In FIG. 1, a horizontal line marks the usual average level of clock gene expression and, starting at about 44 hours following UV exposure, shows typical circadian variation about that line. In contrast, immediately following UVB exposure, levels of gene expression fell to well below normal, and did not return to normal levels for about 20 hours. During that 20 hours, the normal pattern of gene expression was lost for all three genes. And even when levels of gene expression did return to near normal levels, the period from about 20 hours to about 44 hours was required for the normal sinusoidal pattern of expression to return. So UV exposure really had two effects. One effect is the dramatic decline in the level of expression of circadian genes and the other is the pattern, which is to say, the timing of their expression. From 0 to about 44 hours following UV exposure, the timing of DNA and protein synthesis, mitosis and cytokinesis, RNA synthesis and repair and programmed cell death (apoptosis), are all compromised.

Of course, UV exposure occurs during the daytime, especially during the critical 10 a.m. to 2 p.m. window. As already noted, the concentration of PER and CRY proteins in the nucleus peaks at the end of circadian daytime, at which time the CRY proteins act to inhibit transcription of the CLOCK/BMAL1 heterodimer. Any delay in reaching the critical concentration that turns off clock and bmal1 expression, will lengthen the circadian cycle. So, UV exposure tends to lengthen the circadian cycle. This throws the cell cycle out of sync with the environment. DNA replication and mitosis may not occur at night, which is optimal for cell replication. Also, the gating influence that circadian genes exert on the cell cycle may be compromised, so that DNA damage may not be detected or may not be repaired, and may be allowed to pass on to daughter cells.

Sirtuins are Reported to Delay the Onset of Mitosis

Sirtuin 1 (also known as SIRT1 or Silent information regulator two ortholog 1) is an enzyme that regulates metabolism and cell survival in response to stress. It is associated with cell longevity. The sirt1 gene, which encodes for the SIRT1 enzyme, is not a circadian gene. Chua et al. have suggested that SIRT1 promotes replicative senescence by arresting the cell cycle (Chua et al. (2005) Mammalian SIRT1 limits replicative life span in response to chronic genotoxic stress. Cell Metabolism 2, 67-76).

US 2009-0082278 (herein incorporated by reference, in its entirety) further describes this gene and topical skin compositions that may upregulate it. Paragraphs 8-13 read:

"The applicants have recently discovered the involvement of a new protein in the mechanisms of skin cells which has a significant role in the aging process and cell protection."

"The applicants have demonstrated that the SIRT protein, and more precisely the SIRT1 protein, was expressed in skin cells and that its expression was related to different stresses that cutaneous cells encounter. They have demonstrated in particular that the induction of this protein expression, using different agents, allowed for the protection of cells and better helped them to fight against stress and intrinsic aging."

"SIRT proteins are part of the Sirtuin family, and are NAD+ dependent nuclear proteins that play a significant role in histone deacetylation. SIR genes (Silent Information Regulators), which code for SIR proteins, were described for the first time in *S. cerevisiae* in 1979 (Rine J and A l., Genetics 1979). Later, it was demonstrated that an over-expression of the SIR2P protein, in *C. elegans*, allowed the lifespan of the organism to increase (Tissenbaum and A l., Nature 2001). This study has permitted to hypothesize that these proteins are related to longevity."

"The SIRT1 protein is the best characterized human sirtuin and interacts with numerous transcription regulators. The human SIRT1 protein has been described as being involved in p53 regulation (Cheng H L and A 1. Proc Natl Acad Sci USA. 2003), and more recently as a modulator of cell senescence (Langley E and A l., EMBO J. 2002). Other human SIRT proteins have been discovered (SIRT2, SIRT3, SIRT4-7). The human SIRT2 protein has been studied very little; however some studies have demonstrated its role in the control of mitotic activity (Dryden S C and A l. Mol Cell Bio. 2003) as well as its involvement in the regulation of the p53 protein (Vaziri H and A l., Cell. 2001). To date, deacetylase sirtuins are considered a family of enzymes playing an important role in the regulation of cellular death and in its lifecycle (Porcu M. and Chiarugi A, Trends Pharmacol Sci., 2005)."

"The present invention [that is, US 2009-0082278] relates to a cosmetic or pharmaceutical composition comprising, in a cosmetically or pharmaceutically acceptable medium, at least one compound likely to activate the synthesis of SIRT proteins in skin cells. Preferentially, according to the invention, the compounds will activate a particular class of SIRT proteins, the SIRT1 proteins."

"To date, no use of compounds that serve as inductors of the synthesis of the SIRT family of proteins, in skin cells, has ever been described."

The present specification makes the point that, to date, no use of compositions comprising sirt1 activators in concert with circadian gene activators, has ever been described, even in US2009-0082278. To the best of the applicant's knowledge, a topical composition that addresses depressed levels of CLOCK and PER1 proteins in human epidermal keratinocytes, comprising one or more non-circadian, mitosis-delay agents, is unknown.

Topical Compositions for DNA Repair

Topical products for application to skin to promote the cellular repair process are known. For example, such products may include DNA repair enzymes for improving the effectiveness of natural cellular DNA repair, humectant ingredients for maintaining keratinocyte hydration, moisturizing ingredients for improving skin barrier function, and so on. While these ingredients may improve the ability of keratinocytes to repair themselves, there is always room for improvement. In contrast to the prior art, the present invention provides means of restoring the levels of undamaged circadian proteins in skin cells and means of restoring the normal pattern of circadian gene expression, combined with a means of inhibiting damaged DNA from being passed on to daughter cells.

OBJECTS OF THE INVENTION

It is an object of the invention to provide a topical composition that, when applied, restores normal levels of circadian proteins in skin cells and restores the normal pattern of circadian gene expression, in an accelerated fashion.

It is an object of the invention to provide a topical composition that repairs photo damaged and/or oxidatively damaged skin by upregulating clock and per1 gene expression, and by delaying mitosis of skin cells.

It is an object of the invention provide a topical composition that reduces the chance of proliferating damaged skin cell DNA.

It is an object of the invention to provide a topical composition that reduces the chance of proliferating skin cell DNA that has been damaged by environmental aggressors, particularly UV exposure.

It is a further object of the invention to provide a composition for treating skin, comprising at least one keratinocyte clock or per1 gene activator, at least one non-circadian mitosis delay agent and, optionally, at least one DNA repair enzyme.

SUMMARY

All of the foregoing are met by a topical composition comprising at least one agent that upregulates circadian gene expression in skin cells and at least one non-circadian agent that delays mitosis in skin cells. It has been discovered that compositions comprising agents that upregulate (or activate) clock genes and per1 genes, while also increasing the levels of SIRT1, synergistically promote cellular viability, cellular longevity, inhibit cellular damage due to environmental aggressors, improve repair of DNA damage and synergistically reduce the chance of proliferating damaged skin cell DNA. Optionally, the composition comprises one or more DNA repair enzymes.

The preferred embodiments of the present invention are topical skin compositions that manifest the effects described above. Preferably, such compositions comprise one or more keratinocyte clock and per1 gene activators, along with SIRT1 or one or more sirt1 activators. Preferably, such compositions are easy to use, efficacious, cosmetically acceptable, chemically, thermodynamically and light stable, safe for topical use, have little or no side effects, and commercially feasible in a personal care marketplace.

DETAILED DESCRIPTION

Figure 1:
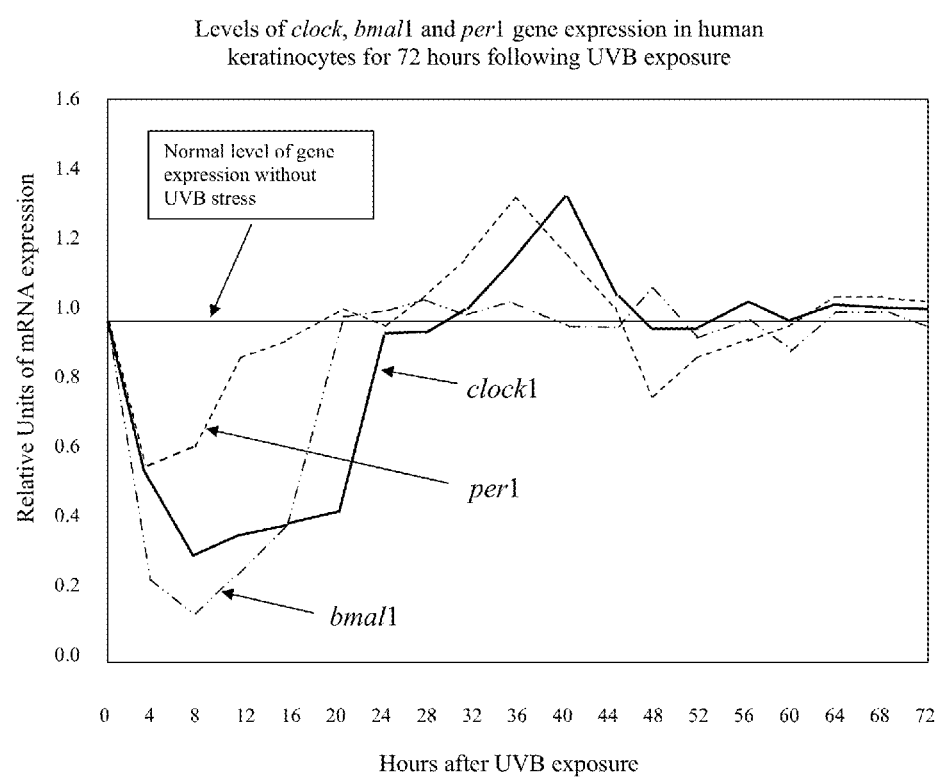
FIG. 1 shows the levels of clock, bmal1 and per1 gene expression in human keratinocytes for 72 hours following UV exposure.

To the best of the applicant's knowledge no use of topical compositions comprising sirt1 activators to promote cell cycle arrest, in concert with topical application of circadian gene activators to restore normal circadian cycle, has ever been described.

Definitions

All percentages mentioned herein are percentages by weight unless otherwise indicated. In relation to genes, the terms "activate" and "upregulate" or etymologically related terms, mean an ingredient that causes the expression of one or more proteins encoded by the gene.

The term "Clock gene" is sometimes used in the literature to refer to any of the so called "canonical" circadian genes, including clock, bmal1, period, and cryptochrome genes. In this specification "clock" (in italics) always refers to the gene that encodes CLOCK proteins. Collectively, the genes clock, bmal1, period, and cryptochrome, are herein referred to as "circadian genes".

The term "DNA repair enzyme" means an enzyme that is able to repair DNA base mutagenic damage. Such enzymes are often categorized by the type of DNA damage they repair. For example, BER (base excision repair) enzymes, nucleotide excision repair (NER) enzymes; mismatch repair (MMR) enzymes; DNA helicases; DNA polymerases, and so on. For example, mutations such as 8-oxo-7,8-dihydro-2'-deoxyguanosine may be repaired by OGG1 (8-oxoGuanine glycosylase. T-T dimers may be repaired by nucleotide excision repair enzyme, Photolyase. 6-4 photoproducts may be repaired by NER. O6-methyl guanine may be repaired by 06-alkyl guanine transferase (AGT).

"Repair", with respect to skin or skin cells, means that keratinocyte viability, strength, and longevity are generally improved. Examples of repair include repairing damaged keratinocyte DNA and reversing a loss of cellular hydration due to UV light, smoke or other environmental aggressors.

"Safe for topical use" means complying with all regional and local regulations that govern the safety of cosmetic products. "Cosmetically acceptable" means that the appearance, feel and smell of a composition is within the limits of acceptability of a consumer, as understood by a person of ordinary skill in the art. "Chemically stable", "thermodynamically stable" and "light stable" mean that from manufacture to a period of at least six months (more preferably 3 years), a composition remains cosmetically acceptable. "Commercially feasible in a personal care marketplace" means that the cost of manufacture and distribution of a composition should not be more than is already experienced in the personal care industry.

CLOCK and PERIOD1 Upregulation

The composition of the invention contains at least one agent that upregulates clock and/or per1 keratinocyte genes. Suggested concentrations of these agents, in total, range from about 0.000001 to about 40%, preferably from about 0.000005 to 35%, more preferably from about 0.00001 to 25%, with respect to the total weight of the final composition. In general, these ranges may be understood to be effective amounts. By "effective amount", we mean that the concentration of these agents, in a topical composition applied to human skin under environmental assault, is sufficient to improve the rate keratinocyte survival by at least 5%. Suitable clock or per1 activators may be present in the form of botanical extracts, polypeptides, peptides, amino acids, and the like.

A particularly preferred clock and/or per1 gene activator comprises a peptide of the formula (I):

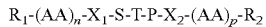

where $(AA)_n$-$X_1$-S-T-P-$X_2$-$(AA)_p$ is (SEQ ID No. 1) and:
$X_1$ represents threonine or serine, or is equal to zero,
$X_2$ represents isoleucine or leucine or proline or valine or alanine or glycine, or is equal to zero,
AA represents any amino acid or derivative thereof, and n and p are whole numbers between 0 and 4 (0 and 4, inclusive)
$R_1$ represents the primary amine function of the N-terminal amino acid, either free or substituted by a protective grouping that may be chosen from either an acetyl group, a benzoyl group, a tosyl group, or a benzyloxycarbonyl group,
$R_2$ represents the hydroxyl group of the carboxyl function of the C-terminal amino acid, substituted by a protective grouping that may be chosen from either a $C_1$ to $C_{20}$ alkyl chain or an $NH_2$, NHY, or NYY group with Y representing a $C_1$ to $C_4$ alkyl chain, and wherein the sequence of general formula (I) comprises from about 3 to 13 amino acid residues.

The sequence of general formula (I) may contain substitutions of amino acids $X_1$ and $X_2$ with other chemically equivalent amino acids, wherein the amino acids are: Alanine (A), Arginine (R), Asparagine (N), Aspartic Acid (D), Cysteine (C), Glutamic Acid (E), Glutamine (Q), Glycine (G), Histidine (H), Isoleucine (I), Leucine (L), Lysine (K), Methionine (M), Phenylalanine (F), Proline (P), Serine (S), Threonine (T), Tryptophan (W), Tyrosine (Y) and Valine (V).

More preferred versions of formula I are peptides, as follows:

```
(SEQ ID No. 2)
Y-V-S-T-P-Y-N-NH2
Tyr-Val-Ser-Thr-Pro-Tyr-Asn-NH2
```

-continued (SEQ ID NO. 3)
NH$_2$-V-S-T-P-E-NH$_2$
NH$_2$-Val-Ser-Thr-Pro-Glu-NH$_2$ S-T-P-NH$_2$
Ser-Thr-Pro-NH$_2$ (SEQ ID No. 4)
NH$_2$-L-H-S-T-P-P-NH$_2$
NH$_2$-Leu-His-Ser-Thr-Pro-Pro-NH$_2$ (SEQ ID No. 5)
CH$_3$NH-R-H-S-T-P-E-NH$_2$
CH$_3$-NH-Arg-His-Ser-Thr-Pro-Glu-NH$_2$ (SEQ ID No. 6)
CH$_3$NH-H-S-T-P-E-CH$_3$NH
CH$_3$-NH-His-Ser-Thr-Pro-Glu-CH$_3$-NH More preferred is the S-T-P-NH$_2$ peptide, SEQ ID No. 4, or mixtures thereof. Most preferred is a peptide manufactured by ISP-Vinscience under the trademark Chronolux® having the INCI name Tripeptide-32.

Figure 2:
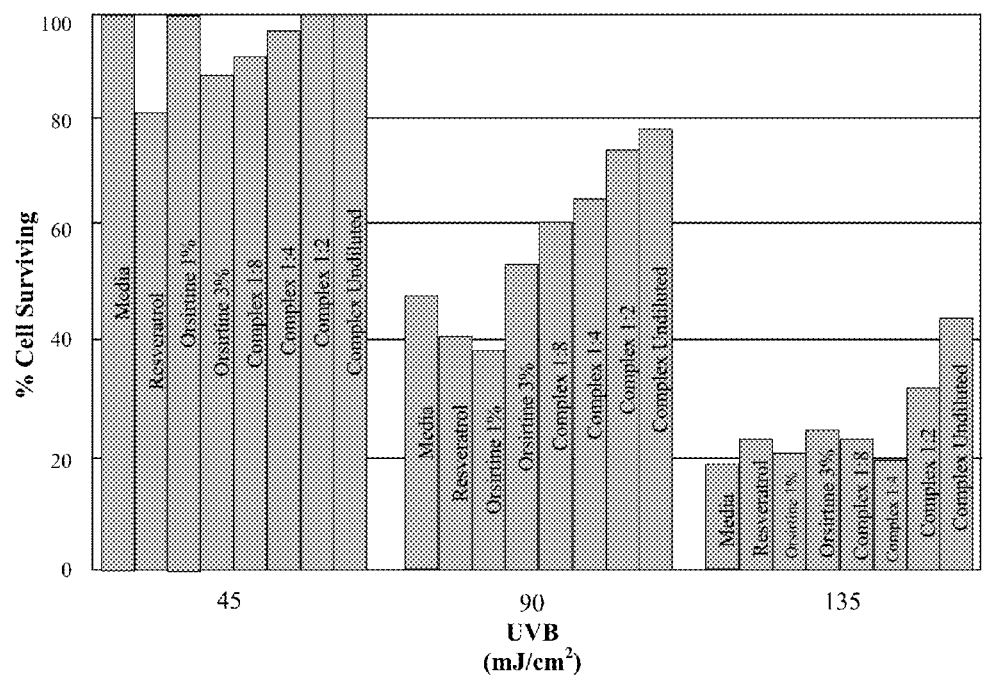
FIG. 2 shows the effect of the sirt1 activators, Orsirtine™ and resveratrol, on human keratinocyte survival.
Figure 3:
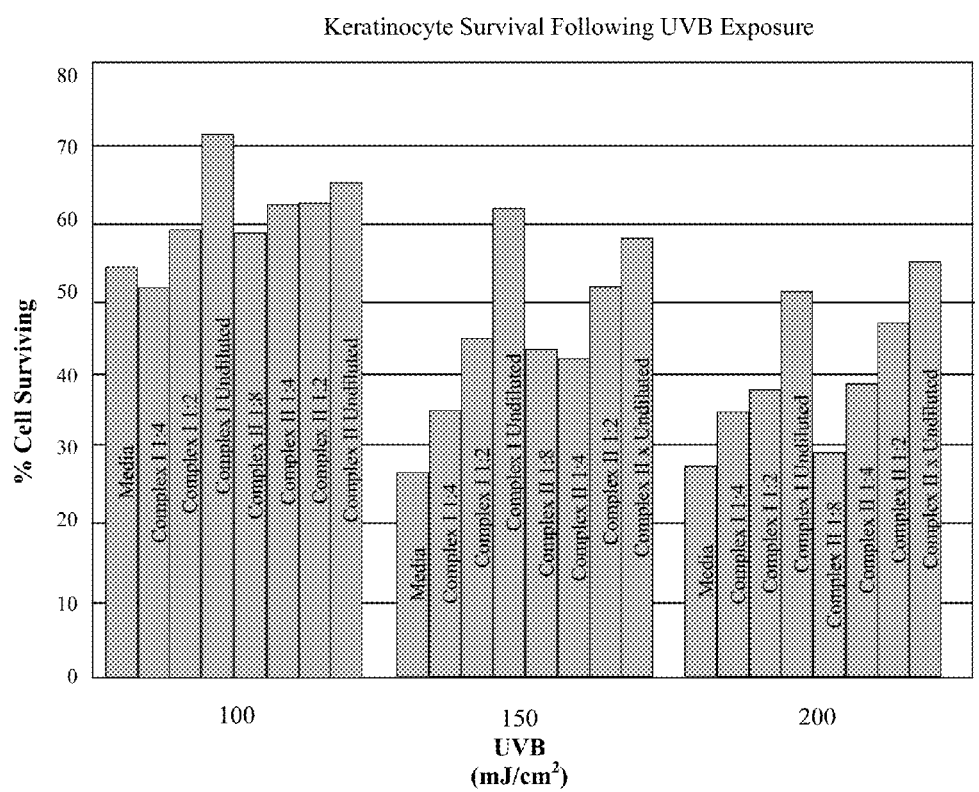
FIG. 3 shows the effect of Circadian Gene Activators in combination with sirt1 activators, Orsirtine™ and resveratrol.

FIGS. 1, 2 and 3 of related application U.S. Ser. No. 12/367,705, and the text describing those figures, demonstrate the ability of Chronolux® to improve keratinocytes survival against UV induced stress, especially when combined with at least one DNA repair enzyme.

It is not immediately obvious that simultaneously applying clock and per1 gene activators would produce a beneficial result. After all, in normal circadian rhythm, cellular concentrations of CLOCK and Period1 protein are out of phase. Nevertheless, a beneficial result is achieved. It may be suggested that skin cells under environmental assault are so depleted in levels of CLOCK and PERIOD1 proteins, that a benefit is achieved by upregulating both proteins as quickly as possible.

SIRTUIN1 Upregulation

We have unexpectedly found, that the beneficial results achieved by the application of clock and per1 keratinocyte gene activators, are modified, sometimes significantly improved, when combined with a keratinocyte sirt1 activator. SIRT1 tends to induce cell cycle arrest. Given the complexity of the circadian mechanism and its regulatory interaction with the cell cycle, it may not have been expected from the prior art that it would be beneficial to induce cell cycle arrest while simultaneously restoring normal levels of circadian proteins.

While not wishing to be bound by any one theory, it will be appreciated that PER1 has direct effects in the cell cycle, other than through circadian oversight. For example, PER1, aside from its role as a core component of the circadian cycle, is reportedly able to activate the ATM kinase pathway leading to cell cycle arrest. ATM (Ataxia telangiectasia mutated) kinase is a nuclear protein kinase that is recruited in response to DNA double stranded breaks. ATM kinase phosphorylates CHK1 and CHK2, cell cycle checkpoint regulators, which are involved in cell cycle arrest and delayed entry into mitosis. When PER1 is under expressed, as a result of some environmental stress, cell cycle arrest may not occur or may be delayed. Thus, there may insufficient time to effect repairs to damaged DNA before mitosis or cytokinesis. At the same time, decreased expression of PER1 has been linked to decreased apoptosis. Thus, a damaged cell that should die, may survive and divide. Therefore, given that environmental stress leads to an abnormal decrease in the levels of PER1, which leads to failure to arrest the cell cycle and decreased apoptosis, which lead to propagation of damaged DNA, one might expect that per1 activation would correct the problem.

Nevertheless, we have observed that keratinocyte viability is significantly improved when a sirt1 gene activator is used in combination with clock and per1 gene activators. While not wishing to be bound by any one theory, this observation may imply that activation of per1 by itself, fails to restore the levels of PER1 fast enough to effect repairs before damaged DNA can be propagated to daughter cells.

By "SIRT1 activator" we mean any compound that is likely to support the endogenous production of SIRT1 proteins, particularly the molecules involved in the positive control of precursors such as DNA or RNA. Among these compounds, which are likely to activate the synthesis of SIRT1 proteins in skin cells, different molecules, such as polyphenols, have been described. More particularly derivatives of trans-stilbene (such as, resveratrol, piceatannol), derivatives of chalcones (such as, isoliquiritigenin, butein), and derivatives of flavones (such as fistein, luteolin, quercetin) can be mentioned. The efficacy of resveratrol or resveratrol derivative, in combination with at least one DNA repair enzyme, has been shown in related application, U.S. Ser. No. 11/837,658. However, certain peptides, due to their inherent structural similarities to peptides in the skin, are preferred sirt1 activators. More preferred still, are a synergistic combination of peptidic activator(s) and resveratrol (more on this, below).

Peptidic Sirt1 Activators

Peptides, due to their inherent structural similarities to peptides in the skin, are preferred sirt1 activators. Among the compounds of peptidic nature, protein fragments, peptidic and polypeptidic fragments, peptides, as well as all sequences of two or more amino acids linked together by peptide bonds can be mentioned. In a preferred embodiment of the present invention, the peptide fragments range in size from 3 to 50 amino acids, more particularly from 3 to 10 amino acids. All of these peptide fragments have biological activity. A preferred peptide is:

(SEQ ID No. 7)
(AA)$_n$-G-L-Y-D-N-L-E-(AA)$_n$(AA)$_n$-Gly-Leu-Tyr-Asp-

Asn-Leu-Glu-(AA)$_n$ wherein (AA) is any particular amino acid or derivative thereof, and n is a whole number between 0 and 3 (0 and 3, inclusive). A particularly preferred peptide is:

(SEQ ID No. 8)
G-L-Y-D-N-L-E Gly-Leu-Tyr-Asp-Asn-Leu-Glu.

This peptide is available as Orsirtine™ GL (INCI name: Water (and) Glycerin (and) Oryza Sativa (Rice) Extract), available from ISP Vincience. In compositions of the present invention, peptidic SIRT1 activators are present in an amount between around 0.000001% and 20%, and preferentially in an amount between about 0.0001 and 5% with respect to the total weight of the final composition.

Resveratrol and Derivatives Thereof

Resveratrol, also referred to as 3,5,4'-trihydroxystilbene, is a polyhydroxy-substituted stilbene compound present in red grapes, raspberries, blueberries, and certain other plant berries or extracts, which has the general formula:

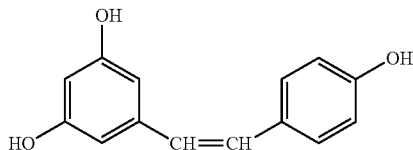

Resveratrol has been shown to be an effective antioxidant and also exhibits strong anti-proliferative and anti-inflammatory properties. It has recently been reported that resveratrol can mimic caloric restriction (CR) in various organisms, such as yeast, roundworms, fruit-flies, short-lived fish, and mice, slow the aging process in such organisms, and significantly extend their life spans. Although not wishing to be bound by any specific theory, inventors of the present invention believe that resveratrol can reduce cell proliferation and slow down the apoptosis process, thereby allowing more time for DNA damage repair in the cells. It is postulated that resveratrol, when combined with a DNA repair enzyme, can result in a synergistic effect on boosting or otherwise enhancing the natural DNA repair capacity of the cells.

However, resveratrol may be potentially unstable in certain cosmetic formulations. Specifically, resveratrol is susceptible to hydrolysis in aqueous-based formulations and may cause such formulations to become discolored. One way to address the instability of resveratrol in aqueous-based formulations is to modify the resveratrol by substituting the hydroxy groups at the 3, 5, and 4' position with other functional groups to form resveratrol derivatives that are more stable in cosmetic formulas. Such derivatives are preferred over resveratrol. It has been discovered that resveratrol derivatives of inorganic acids, organic carboxylic acids, mono-, di-, or polysaccharides, or other functional groups are more stable in aqueous-based formulations. The substitution groups function to protect and stabilize the phenol groups of resveratrol and make the resveratrol derivative more suitable for use in aqueous-based cosmetic formulations. The substitution groups can also be hydrolyzed easily, from the compound upon application to the skin, preferably by enzymes and other ingredients on the skin surface, to release an active form of resveratrol into the skin. The resveratrol derivatives of the present invention have a general formula of:

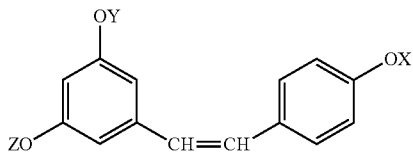

wherein X, Y, and Z are either hydrogen or a protective group, provided that at least one of X, Y, and Z is the protective group. Exemplary resveratrol derivatives suitable for use in the cosmetic or topical compositions of the present invention are described in greater detail hereinafter.

A. Resveratrol Esters of Inorganic or Organic Acids

Resveratrol esters of inorganic acids, in which one or more of the X, Y, and Z are inorganic acid functional groups such as phosphates, nitrates, sulfonates, and carbonates, can be used in the present invention. Following is a list of exemplary inorganic acid esters that are particularly suitable for practice of the present invention:

| | |
|---|---|
| 3-phosphate-5,4'-dihydroxystilbene | 5-phosphate-3,4'-dihydroxystilbene |
| 4'-phosphate-3,5-dihydroxystilbene | 3,5-diphsophate-4'-hydroxystilbene |
| 3,4'-diphosphate-5-hydroxystilbene | 4',5-diphosphate-3-hydroxystilbene |
| 3,5,4'-triphosphate stilbene | 3-nitrate-5,4'-dihydroxystilbene |
| 5-nitrate-3,4'-dihydroxystilbene | 4'-nitrate-3,5-dihydroxystilbene |
| 3,5-dinitrate-4'-hydroxystilbene | 3,4'-dinitrate-5-hydroxystilbene |
| 4',5-dinitrate-3-hydroxystilbene | 3,5,4'-trinitrate stilbene |
| 3-sulfonate-5,4'-dihydroxystilbene | 5-sulfonate-3,4'-dihydroxystilbene |
| 4'-sulfonate-3,5-dihydroxystilbene | 3,5-disulfonate-4'-hydroxystilbene |
| 3,4'-disulfonate-5-hydroxystilbene | 4',5-disulfonate-3-hydroxystilbene |
| 3,5,4'-trisulfonate stilbene | 3-carbonate-5,4'-dihydroxystilbene |
| 5-carbonate-3,4'-dihydroxystilbene | 4'-carbonate-3,5-dihydroxystilbene |
| 3,5-dicarbonate-4'-hydroxystilbene | 3,4'-dicarbonate-5-hydroxystilbene |
| 4',5-dicarbonate-3-hydroxystilbene | 3,5,4'-tricarbonate stilbene. |

Pharmaceutically acceptable salts of the above-listed resveratrol esters can also be used in the cosmetic compositions of the present invention. Such salts may include one or more monovalent or divalent cations selected from the group consisting of Na, K, Mg, Ca, Fe, and $NH_4$. The salts can be formed by adding corresponding bases, such as sodium hydroxide, potassium hydroxide, and the like, into a solution containing the resveratrol esters.

The inorganic acid esters of resveratrol may be readily formed by well known chemical processes that substitute the hydroxyl groups of phenols or polyphenols with the phosphate, sulfonates, and carbonate functional groups. For example, U.S. Pat. No. 4,003,966 describes a one-step process for selectively phosphorylating phenols to form phosphate esters thereof, the contents of which are hereby incorporated herein by reference in their entireties for all purposes.

A particularly preferred resveratrol derivative for practice of the present invention is the 3,4',5-triphosphate stilbene, also referred to as a resveratrol triphosphate ester having the formula:

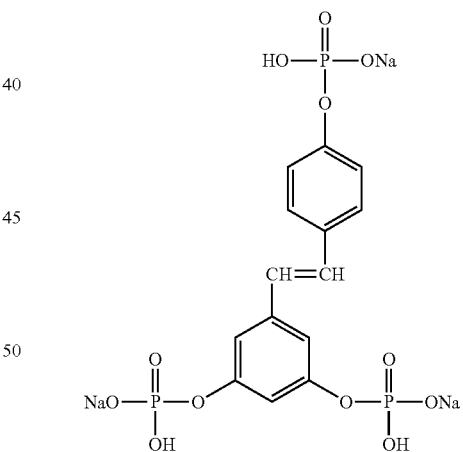

Phosphate esters of resveratrol, including resveratrol triphosphate, are disclosed in International Patent Application Publication No. WO 2006/029484A1, which is hereby incorporated by reference in its entirety. Resveratrol triphosphate may be synthesized by the method as set forth in Example 2 of WO 2006/029484A1. More specifically, a solution of resveratrol (3,4,5-trihydroxystilbene) (25 mmols, 5.7 grams) and dimethylaminopyridine (7.5 mmols, 0.93 grams) in 100 ml acetonitrile is cooled under nitrogen up to −10° C. After 10 minutes, carbon tetrachloride (375 mmol, 36.2 ml) and DIEA (159 mmol; 27.7 ml) and the mixture maintained under stirring for 30 minutes. Dibenzylphosphate (113 mmols, 25.0 ml) is added and the mixture stirred for an additional 12 hours at room temperature. The course of the reaction is monitored by TLC (silica F254, eluent ethyl acetate/n-hexane 80/20 v/v). One liter of 0.5 M KH2PO4 is added, and the mixture then extract with ethyl acetate. The resulting product, tri (dibenzylphosphate) resveratrol, is purified by filtration on a silica gel, washing first with a mixture of ethyl acetate/n-hexane (80/20 v/v) to remove any remaining unreacted resveratrol, and then with methanol, to obtain a yellow oil.

To the tri(dibenzylphosphate) resveratrol (12.5 mmol) in 200 mL of anhydrous DCM at 0° C., is added bromomethylsilane (79 mmols, 10.4 mL). After 2 hours, 300 mL of H2O is added, and the reaction mixture is stirred for 1 hour. The water phase is washed again with ethyl acetate, then lyophilized to obtain an orange oil.

To the product obtained above, solubilized in 400 mL of ethanol, is added CH3ONa (37 mmol; 2.03 g) and the reaction stirred for 12 hours at room temperature. The ethanol is evaporated in a rotavapor, and the residue solubilized in H2O. The water phase is washed with ethyl acetate and lyophilized. The mass spectrum of the resulting white solid shows the presence of resveratrol triphosphate (PM=468.1), with a total yield of >90% with respect to resveratrol.

If desired, the resveratrol triphosphate may be neutralized with organic or inorganic bases such as sodium hydroxide, potassium hydroxide and the like. Particularly preferred is where the resveratrol triphosphate is neutralized with sodium hydroxide to form trisodium resveratrol triphosphate. Resveratrol triphosphate may also be purchased from Ajinomoto in the neutralized form, having the CTFA trisodium resveratrol triphosphate.

B. Carboxylic Acid Esters of Resveratrol

Another group of resveratrol derivatives that can be used in the present invention is esters of resveratrol and aliphatic or aromatic carboxylic acids, in which one or more of X, Y, and Z is a —C(O)—$R_1$ group, wherein $R_1$ is selected from the group consisting of linear, branched, saturated or unsaturated, or cyclic $C_1$-$C_{40}$ alkyl, substituted $C_1$-$C_{40}$ alkyl, $C_1$-$C_{40}$ alkenyl, substituted $C_1$-$C_{40}$ alkenyl, $C_1$-$C_{40}$ alkynyl, substituted $C_1$-$C_{40}$ alkynyl, aryl, $C_1$-$C_{40}$ aryl, and $C_1$-$C_{40}$ substituted aryl. In one preferred embodiment, the R group is a straight or branched chain fatty, or $C_{6-30}$, saturated or unsaturated alkyl group. The substituents may be selected from $C_{1-40}$ straight or branched chain, saturated or unsaturated alkyl, halogen (such as fluoro), hydrogen, alkoxy, hydroxyl, and the like.

Exemplary carboxylic acids that can be used to form ester of resveratrol include, but are not limited to: saturated monocarboxylic acids, such as acetic acid, propionic acid, butyric acid (C4), valeric acid, hexanoic acid, caprylic acid (C8), lauric acid, stearic acid (C18), isostearic acid (branched C18), linoleic acid, linolenic acid, myristic acid (C14), arachidic acid (C20), arachidonic acid, erucic acid, behenic acid (C22), lauric acid (C12), capric acid (C10), caproic (C6), and palmitic acid (C16); unsaturated monocarboxylic acids, such as acrylic acid, methacrylic acid, sorbic acid, oleic acid, linoleic acid, linolenic acid, docosahexaenoic acid, and eicosapentaenoic acid; amino acids, such as arginine, glutamine, and tyrosine; keto acids, such as pyruvic acid and acetoacetic acid; aromatic carboxylic acids, such as ascorbic acid, benzoic acid, salicylic acid, and ferulic acid; di- and tri-carboxylic acids, such as oxalic acid, malonic acid, malic acid, succinic acid, and glutaric acid. The designation "C" followed by a number indicates the number of carbon atoms in the alkyl chain.

Following is a list of exemplary carboxylic acid esters of resveratrol that are particularly suitable for practice of the present invention:

| | |
|---|---|
| 3-acetate-5,4'-dihydroxystilbene | 5-acetate-3,4'-dihydroxystilbene |
| 4'-acetate-3,5-dihydroxystilbene | 3,5-diacetate-4'-hydroxystilbene |
| 3,4'-diacetate-5-hydroxystilbene | 4',5-diacetate-3-hydroxystilbene |
| 3,5,4'-triacetate stilbene | 3-propionate-5,4'-dihydroxystilbene |
| 5-propionate-3,4'-dihydroxystilbene | 4'-propionate-3,5-dihydroxystilbene |
| 3,5-dipropionate-4'-hydroxystilbene | 3,4'-dipropionate-5-hydroxystilbene |
| 4',5-dipropionate-3-hydroxystilbene | 3,5,4'-tripropionate stilbene |
| 3-butyrate-5,4'-dihydroxystilbene | 5-butyrate-3,4'-dihydroxystilbene |
| 4'-butyrate-3,5-dihydroxystilbene | 3,5-dibutyrate-4'-hydroxystilbene |
| 3,4'-dibutyrate-5-hydroxystilbene | 4',5-dibutyrate-3-hydroxystilbene |
| 3,5,4'-tributyrate stilbene | 3-valerate-5,4'-dihydroxystilbene |
| 5-valerate-3,4'-dihydroxystilbene | 4'-valerate-3,5-dihydroxystilbene |
| 3,5-divalerate-4'-hydroxystilbene | 3,4'-divalerate-5-hydroxystilbene |
| 4',5-divalerate-3-hydroxystilbene | 3,5,4'-trivalerate stilbene |
| 3-hexanoate-5,4'-dihydroxystilbene | 5-hexanoate-3,4'-dihydroxystilbene |
| 4'-hexanoate-3,5-dihydroxystilbene | 3,5-dihexanoate-4'-hydroxystilbene |
| 3,4'-dihexanoate-5-hydroxystilbene | 4',5-dihexanoate-3-hydroxystilbene |
| 3,5,4'-trihexanoate stilbene | 3-caprylate-5,4'-dihydroxystilbene |
| 5-caprylate-3,4'-dihydroxystilbene | 4'-caprylate-3,5-dihydroxystilbene |
| 3,5-dicaprylate-4'-hydroxystilbene | 3,4'-dicaprylate-5-hydroxystilbene |
| 4',5-dicaprylate-3-hydroxystilbene | 3,5,4'-tricaprylate stilbene |
| 3-laurate-5,4'-dihydroxystilbene | 5-laurate-3,4'-dihydroxystilbene |
| 4'-laurate-3,5-dihydroxystilbene | 3,5-dilaurate-4'-hydroxystilbene |
| 3,4'-dilaurate-5-hydroxystilbene | 4',5-dilaurate-3-hydroxystilbene |
| 3,5,4'-trilaurate stilbene | 3-stearate-5,4'-dihydroxystilbene |
| 5-stearate-3,4'-dihydroxystilbene | 4'-stearate-3,5-dihydroxystilbene |
| 3,5-distearate-4'-hydroxystilbene | 3,4'-distearate-5-hydroxystilbene |
| 4',5-distearate-3-hydroxystilbene | 3,5,4'-tristearate stilbene |
| 3-palmitate-5,4'-dihydroxystilbene | 5-palmitate-3,4'-dihydroxystilbene |
| 4'-palmitate-3,5-dihydroxystilbene | 3,5-dipalmitate-4'-hydroxystilbene |
| 3,4'-dipalmitate-5-hydroxystilbene | 4',5-dipalmitate-3-hydroxystilbene |
| 3,5,4'-tripalmitate stilbene | 3-acrylate-5,4'-dihydroxystilbene |
| 5-acrylate-3,4'-dihydroxystilbene | 4'-acrylate-3,5-dihydroxystilbene |
| 3,5-diacrylate-4'-hydroxystilbene | 3,4'-diacrylate-5-hydroxystilbene |
| 4',5-diacrylate-3-hydroxystilbene | 3,5,4'-triacrylate stilbene |
| 3-methacrylate-5,4'-dihydroxystilbene | 5-methacrylate-3,4'-dihydroxystilbene |
| 4'-methacrylate-3,5-dihydroxystilbene | 3,5-dimethacrylate-4'-hydroxystilbene |

-continued 3,4'-dimethacrylate-5-hydroxystilbene
3,5,4'-trimethacrylate stilbene
5-sorbate-3,4'-dihydroxystilbene
3,5-disorbate-4'-hydroxystilbene
4',5-disorbate-3-hydroxystilbene
3-oleate-5,4'-dihydroxystilbene
4'-oleate-3,5-dihydroxystilbene
3,4'-dioleate-5-hydroxystilbene
3,5,4'-trioleate stilbene
5-linoleate-3,4'-dihydroxystilbene
3,5-dilinoleate-4'-hydroxystilbene
4',5-dilinoleate-3-hydroxystilbene
3-linolenate-5,4'-dihydroxystilbene
4'-linolenate-3,5-dihydroxystilbene
3,4'-dilinolenate-5-hydroxystilbene
3,5,4'-trilinolenate stilbene
5-docosahexaenoate-3,4'-dihydroxystilbene
3,5-didocosahexaenoate-4'-hydroxystilbene
4',5-didocosahexaenoate-3-hydroxystilbene
3-eicosapentaenoic-5,4'-dihydroxystilbene
4'-eicosapentaenoic-3,5-dihydroxystilbene
3,4'-dieicosapentaenoic-5-hydroxystilbene
3,5,4'-trieicosapentaenoic stilbene
5-arginate-3,4'-dihydroxystilbene
3,5-diarginate-4'-hydroxystilbene
4',5-diarginate-3-hydroxystilbene
3-glutamate-5,4'-dihydroxystilbene
4'-glutamate-3,5-dihydroxystilbene
3,4'-diglutamate-5-hydroxystilbene
3,5,4'-triglutamate stilbene
5-tyrosate-3,4'-dihydroxystilbene
3,5-dityrosate-4'-hydroxystilbene
4',5-dityrosate-3-hydroxystilbene
3-pyruvate-5,4'-dihydroxystilbene
4'-pyruvate-3,5-dihydroxystilbene
3,4'-dipyruvate-5-hydroxystilbene
3,5,4'-tripyruvate stilbene
5-acetoacetate-3,4'-dihydroxystilbene
3,5-diacetoacetate-4'-hydroxystilbene
4',5-diacetoacetate-3-hydroxystilbene
3-ascorbate-5,4'-dihydroxystilbene
4'-ascorbate-3,5-dihydroxystilbene
3,4'-diascorbate-5-hydroxystilbene
3,5,4'-triascorbate stilbene
5-benzoate-3,4'-dihydroxystilbene
3,5-dibenzoate-4'-hydroxystilbene
4',5-dibenzoate-3-hydroxystilbene
3-salicylate-5,4'-dihydroxystilbene
4'-salicylate-3,5-dihydroxystilbene
3,4'-disalicylate-5-hydroxystilbene
3,5,4'-trisalicylate stilbene
5-ferulate-3,4'-dihydroxystilbene
3,5-diferulate-4'-hydroxystilbene
4',5-diferulate-3-hydroxystilbene
3-oxalate-5,4'-dihydroxystilbene
4'-oxalate-3,5-dihydroxystilbene
3,4'-dioxalate-5-hydroxystilbene
3,5,4'-trioxalate stilbene
5-malonate-3,4'-dihydroxystilbene
3,5-dimalonate-4'-hydroxystilbene
4',5-dimalonate-3-hydroxystilbene
3-malate-5,4'-dihydroxystilbene
4'-malate-3,5-dihydroxystilbene
3,4'-dimalate-5-hydroxystilbene
3,5,4'-trimalate stilbene
5-succinate-3,4'-dihydroxystilbene
3,5-disuccinate-4'-hydroxystilbene
4',5-disuccinate-3-hydroxystilbene
3-glutarate-5,4'-dihydroxystilbene
4'-glutarate-3,5-dihydroxystilbene
3,4'-diglutarate-5-hydroxystilbene
3,5,4'-triglutarate stilbene
5-glutarate-3,4'-dihydroxystilbene
3,5-diglutarate-4'-hydroxystilbene
4',5-diglutarate-3-hydroxystilbene
4',5-dimethacrylate-3-hydroxystilbene
3-sorbate-5,4'-dihydroxystilbene
4'-sorbate-3,5-dihydroxystilbene
3,4'-disorbate-5-hydroxystilbene
3,5,4'-trisorbate stilbene
5-oleate-3,4'-dihydroxystilbene
3,5-dioleate-4'-hydroxystilbene
4',5-dioleate-3-hydroxystilbene
3-linoleate-5,4'-dihydroxystilbene
4'-linoleate-3,5-dihydroxystilbene
3,4'-dilinoleate-5-hydroxystilbene
3,5,4'-trilinoleate stilbene
5-linolenate-3,4'-dihydroxystilbene
3,5-dilinolenate-4'-hydroxystilbene
4',5-dilinolenate-3-hydroxystilbene
3-docosahexaenoate-5,4'-dihydroxystilbene
4'-docosahexaenoate-3,5-dihydroxystilbene
3,4'-didocosahexaenoate-5-hydroxystilbene
3,5,4'-tridocosahexaenoate stilbene
5-eicosapentaenoic-3,4'-dihydroxystilbene
3,5-dieicosapentaenoic-4'-hydroxystilbene
4',5-dieicosapentaenoic-3-hydroxystilbene
3-arginate-5,4'-dihydroxystilbene
4'-arginate-3,5-dihydroxystilbene
3,4'-diarginate-5-hydroxystilbene
3,5,4'-triarginate stilbene
5-glutamate-3,4'-dihydroxystilbene
3,5-diglutamate-4'-hydroxystilbene
4',5-diglutamate-3-hydroxystilbene
3-tyrosate-5,4'-dihydroxystilbene
4'-tyrosate-3,5-dihydroxystilbene
3,4'-dityrosate-5-hydroxystilbene
3,5,4'-trityrosate stilbene
5-pyruvate-3,4'-dihydroxystilbene
3,5-dipyruvate-4'-hydroxystilbene
4',5-dipyruvate-3-hydroxystilbene
3-acetoacetate-5,4'-dihydroxystilbene
4'-acetoacetate-3,5-dihydroxystilbene
3,4'-diacetoacetate-5-hydroxystilbene
3,5,4'-triacetoacetate stilbene
5-ascorbate-3,4'-dihydroxystilbene
3,5-diascorbate-4'-hydroxystilbene
4',5-diascorbate-3-hydroxystilbene
3-benzoate-5,4'-dihydroxystilbene
4'-benzoate-3,5-dihydroxystilbene
3,4'-dibenzoate-5-hydroxystilbene
3,5,4'-tribenzoate stilbene
5-salicylate-3,4'-dihydroxystilbene
3,5-disalicylate-4'-hydroxystilbene
4',5-disalicylate-3-hydroxystilbene
3-ferulate-5,4'-dihydroxystilbene
4'-ferulate-3,5-dihydroxystilbene
3,4'-diferulate-5-hydroxystilbene
3,5,4'-triferulate stilbene
5-oxalate-3,4'-dihydroxystilbene
3,5-dioxalate-4'-hydroxystilbene
4',5-dioxalate-3-hydroxystilbene
3-malonate-5,4'-dihydroxystilbene
4'-malonate-3,5-dihydroxystilbene
3,4'-dimalonate-5-hydroxystilbene
3,5,4'-trimalonate stilbene
5-malate-3,4'-dihydroxystilbene
3,5-dimalate-4'-hydroxystilbene
4',5-dimalate-3-hydroxystilbene
3-succinate-5,4'-dihydroxystilbene
4'-succinate-3,5-dihydroxystilbene
3,4'-disuccinate-5-hydroxystilbene
3,5,4'-trisuccinate stilbene
5-glutarate-3,4'-dihydroxystilbene
3,5-diglutarate-4'-hydroxystilbene
4',5-diglutarate-3-hydroxystilbene
3-glutarate-5,4'-dihydroxystilbene
4'-glutarate-3,5-dihydroxystilbene
3,4'-diglutarate-5-hydroxystilbene
3,5,4'-triglutarate stilbene.

One particularly preferred group of carboxylic acid esters of resveratrol is either saturated or unsaturated fatty acid esters of resveratrol, such as resveratrol butyrates, resveratrol valerates, resveratrol hexanoates, resveratrol sorbates, resveratrol laurates, resveratrol stearates, resveratrol palmitates, resveratrol oleates, resveratrol linoleates, resveratrol linolenates, resveratrol eicosapentaenoates, and resveratrol docosahexanoates. Such fatty acid esters of resveratrol can be readily formed by esterification of resveratrol with acid derivatives according to the Schotten-Baumann reaction in alkaline aqueous medium, as described by U.S. Pat. No. 6,572,882, the content of which is incorporated herein by reference in its entireties for all purposes.

Another particularly preferred group of carboxylic acid esters of resveratrol are the aromatic carboxylic acid esters of resveratrol, such as resveratrol ferulates, which can be formed by reacting resveratrol with ferulic acid in aqueous medium.

C. Resveratrol Ether Derivatives

Yet another group of resveratrol derivatives that can be used in the present invention are resveratrol ethers, in which one or more of X, Y, and Z is —$R_2$, wherein $R_2$ is selected from the group consisting of linear, branched or cyclic $C_1$-$C_{40}$ alkyl, substituted $C_1$-$C_{40}$ alkyl, $C_1$-$C_{40}$ alkenyl, substituted $C_1$-$C_{40}$ alkenyl, $C_1$-$C_{40}$ alkynyl, substituted $C_1$-$C_{40}$ alkynyl, $C_1$-$C_{40}$ aryl, substituted $C_1$-$C_{40}$ aryl, and mono-, di-, oligo-, and polysaccharides. Following is a list of exemplary resveratrol ethers that are particularly suitable for practice of the present invention:

| | |
|---|---|
| 3-methoxy-5,4'-dihydroxystilbene | 5-methoxy-3,4'-dihydroxystilbene |
| 4'-methoxy-3,5-dihydroxystilbene | 3,5-dimethoxy-4'-hydroxystilbene |
| 3,4'-dimethoxy-5-hydroxystilbene | 4',5-dimethoxy-3-hydroxystilbene |
| 3,5,4'-trimethoxy stilbene | 3-ethoxy-5,4'-dihydroxystilbene |
| 5-ethoxy-3,4'-dihydroxystilbene | 4'-ethoxy-3,5-dihydroxystilbene |
| 3,5-diethoxy-4'-hydroxystilbene | 3,4'-diethoxy-5-hydroxystilbene |
| 4',5-diethoxy-3-hydroxystilbene | 3,5,4'-triethoxy stilbene |
| 3-propyloxy-5,4'-dihydroxystilbene | 5-propyloxy-3,4'-dihydroxystilbene |
| 4'-propyloxy-3,5-dihydroxystilbene | 3,5-dipropyloxy-4'-hydroxystilbene |
| 3,4'-dipropyloxy-5-hydroxystilbene | 4',5-dipropyloxy-3-hydroxystilbene |
| 3,5,4'-tripropyloxy stilbene | 3-phenyloxy-5,4'-dihydroxystilbene |
| 5-phenyloxy-3,4'-dihydroxystilbene | 4'-phenyloxy-3,5-dihydroxystilbene |
| 3,5-diphenyloxy-4'-hydroxystilbene | 3,4'-diphenyloxy-5-hydroxystilbene |
| 4',5-diphenyloxy-3-hydroxystilbene | 3,5,4'-triphenyloxy stilbene |
| 3-glucoside-5,4'-dihydroxystilbene | 5-glucoside-3,4'-dihydroxystilbene |
| 4'-glucoside-3,5-dihydroxystilbene | 3,5-diglucoside-4'-hydroxystilbene |
| 3,4'-diglucoside-5-hydroxystilbene | 4',5-diglucoside-3-hydroxystilbene |
| 3,5,4'-triglucoside stilbene. | |

In one specific embodiment of the present invention, a methoxy-substituted resveratrol derivative is used. For example, the compositions of the present invention may comprise 3,5-dimethoxy-4'-hydroxystilbene, which can be extracted from the Indian Kino Tree (*Pterocarpus marsupium*) and is commercially available under the trade name PTEROSTILBENE from Sigma-Aldrich at St. Louis, Mo.

In another specific embodiment of the present invention, the resveratrol derivative contains one or more saccharide-containing protective groups, such as glucose, galactose, mannose, fructose, sucrose, lactose, maltose, trehalose, and the like. For example, resveratrol glucoside, which can be obtained by extraction from plants or plant material such as polygonum cuspidatum tissue or in vitro cultures of vitis vinifera cells, is used in the cosmetic compositions of the present invention.

D. Nitrogen-Containing Derivatives of Resveratrol

The resveratrol derivatives used in the compositions of the present invention may also contain one or more nitrogen-containing functional groups, i.e., one or more of A, B, and C in the above formula are selected from the group consisting of amides, amines, imines, amidines, and carboxamidines. Following is a list of exemplary resveratrol ethers that are particularly suitable for practice of the present invention:

| | |
|---|---|
| 3-amide-5,4'-dihydroxystilbene | 5-amide-3,4'-dihydroxystilbene |
| 4'-amide-3,5-dihydroxystilbene | 3,5-diamide-4'-hydroxystilbene |
| 3,4'-diamide-5-hydroxystilbene | 4',5-diamide-3-hydroxystilbene |
| 3,5,4'-triamide stilbene | 3-amino-5,4'-dihydroxystilbene |
| 5-amino-3,4'-dihydroxystilbene | 4'-amino-3,5-dihydroxystilbene |
| 3,5-diamino-4'-hydroxystilbene | 3,4'-diamino-5-hydroxystilbene |
| 4',5-diamino-3-hydroxystilbene | 3,5,4'-triamino stilbene |
| 3-imino-5,4'-dihydroxystilbene | 5-imino-3,4'-dihydroxystilbene |
| 4'-imino-3,5-dihydroxystilbene | 3,5-diimino-4'-hydroxystilbene |
| 3,4'-diimino-5-hydroxystilbene | 4',5-diimino-3-hydroxystilbene |
| 3,5,4'-triimino stilbene | 3-amidino-5,4'-dihydroxystilbene |
| 5-amidino-3,4'-dihydroxystilbene | 4'-amidino-3,5-dihydroxystilbene |
| 3,5-diamidino-4'-hydroxystilbene | 3,4'-diamidino-5-hydroxystilbene |
| 4',5-diamidino-3-hydroxystilbene | 3,5,4'-triamidino stilbene. |

Preferably, but not necessarily, the resveratrol derivatives of the present invention, when present, are encapsulated in liposomes, either alone or in combination with the DNA repair enzyme and/or one or more additional skin care actives, for more effective delivery thereof into the dermis of skin. The resveratrol derivatives may be present in the cosmetic composition of the present invention at an amount ranging from about 0.001% to about 95%, preferably from about 0.005% to about 90%, more preferably from about 0.1% to about 20%, by total weight of the total composition.

DNA Repair Enzymes

Compositions of the present invention optionally contain at least one DNA repair enzyme. This is unlike U.S. Ser. No. 11/837,658, wherein at least one DNA repair enzyme is required and which does not contemplate the use of a sirt1 activator. Suggested concentrations of the optional DNA repair enzyme are from about 0.00001 to about 35%, preferably from about 0.00005 to about 30%, more preferably from about 0.0001 to about 25%, with respect to the total weight of the final composition.

DNA repair enzymes as disclosed in U.S. Pat. Nos. 5,077,211; 5,190,762; 5,272,079; and 5,296,231, all of which are hereby incorporated by reference in their entirety, are suitable for use in the compositions and method of the invention. One example of such a DNA repair enzyme may be purchased from AGI/Dermatics under the trade name Roxisomes®, and has the INCI name *Arabidopsis Thaliana* extract. It may be present alone or in admixture with lecithin and water. This DNA repair enzyme is known to be effective in repairing 8-oxo-diGuanine base mutation damage.

Another type of DNA repair enzyme that may be used is one that is known to be effective in repairing 06-methyl guanine base mutation damage. It is sold by AGI/Dermatics under the tradename Adasomes®, and has the INCI name *Lactobacillus* ferment, which may be added to the composition of the invention by itself or in admixture with lecithin and water.

Another type of DNA repair enzyme that may be used is one that is known to be effective in repairing T-T dimers. The enzymes are present in mixtures of biological or botanical materials. Examples of such ingredients are sold by AGI/Dermatics under the tradenames Ultrasomes® or Photosomes®. Ultrasomes® comprises a mixture of *Micrococcus* lysate (an end product of the controlled lysis of various species of *micrococcus*), lecithin, and water. Photosomes® comprises a mixture of plankton extract (which is the extract of marine biomass which includes one or more of the following organisms: thalassoplankton, green micro-algae, diatoms, greenish-blue and nitrogen-fixing seaweed), water, and lecithin.

Another type of DNA repair enzyme may be a component of various inactivated bacterial lysates such as *Bifida* lysate or *Bifida* ferment lysate, the latter a lysate from *Bifido* bacteria which contains the metabolic products and cytoplasmic fractions when *Bifido* bacteria are cultured, inactivated and then disintegrated. This material has the INCI name *Bifida* Ferment Lysate.

Other suitable DNA repair enzymes include Endonuclease V, which may be produced by the denV gene of the bacteriophage T4. Also suitable are T4 endonuclease; $O^6$-methylguanine-DNA methyltransferases; photolyases such as uracil- and hypoxanthine-DNA glycosylases; apyrimidinic/apurinic endonucleases; DNA exonucleases, damaged-bases glycosylases (e.g., 3-methyladenine-DNA glycosylase); correndonucleases either alone or in complexes (e.g., *E. coli* uvrA/uvrB/uvrC endonuclease complex); APEX nuclease, which is a multi-functional DNA repair enzyme often referred to as "APE"; dihydrofolate reductase; terminal transferase; topoisomerase; $O^6$ benzyl guanine; DNA glycosylases.

Other types of suitable DNA repair enzymes may be categorized by the type of repair facilitated and include BER (base excision repair) or BER factor enzymes such as uracil-DNA glycosylase (UNG); single strand selective monofunctional uracil DNA glycosylase (SMUG1); 3,N(4)-ethenocytosine glycosylase (MBD4); thymine DNA-glycosylase (TDG); A/G-specific adenine DNA glycosylase (MUTYH); 8-oxoguanine DNA glycosylase (OGG1); endonuclease III-like (NTHL1); 3-methyladenine DNA glycosidase (MPG); DNA glycosylase/AP lyase (NEIL1 or 2); AP endonuclease (APEX 1 and 2), DNA ligase (LIG3), ligase accessory factor (XRCC1); DNA 5'-kinase/3'-phosphatase (PNKP); ADP-ribosyltransferase (PARP1 or 2).

Another category of DNA repair enzymes includes those that are believed to directly reverse damage such as $O^6$-MeG alkyl transferase (MGMT); 1-meA dioxygenase (ALKBH2 or ALKBH3).

Yet another category of enzymes operable to repair DNA/protein crosslinks includes Tyr-DNA phosphodiesterase (TDP1).

Also suitable are MMR (mismatch exision repair) DNA repair enzymes such as MutS protein homolog (MSH2); mismatch repair protein (MSH3); mutS homolog 4 (MSH4); MutS homolog 5 (MSH5); or G/T mismatch-binding protein (MSH6); DNA mismatch repair protein (PMS1, PMS2, MLH1, MLH3); Postmeiotic segregation increased 2-like protein (PMS2L3); or postmeiotic segregation increased 2-like 4 pseudogene (PMS2L4).

Also suitable are DNA repair enzymes are those known as nucleotide excision repair (NER) enzymes and include those such as Xeroderma pigmentosum group C-complementing protein (XPC); RAD23 (*S. cerevisiae*) homolog (RAD23B); caltractin isoform (CETN2); RFA Protein 1, 2, of 3 (RPA1, 2, or 3); 3' to 5' DNA helicase (ERCC3); 5' to 3' DNA helicase (ERCC2); basic transcription factor (GTF2H1, GTF2H2, GTF2H3, GTF2H4, GTF2H5); CDK activating kinase (CDK7, CCNH); cyclin G1-interacting protein (MNAT1); DNA excision repair protein ERCC-51; excision repair cross-complementing 1 (ERCC1); DNA ligase 1 (LIG1); ATP-dependent helicase (ERCC6); and the like.

Also suitable may be DNA repair enzymes in the category that facilitate homologous recombination and include, but are not limited to DNA repair protein RAD51 homolog (RAD51, RAD51L1, RAD51B etc.); DNA repair protein XRCC2; DNA repair protein XRCC3; DNA repair protein RAD52; ATPase (RAD50); 3' exonuclease (MRE11A); and so on.

DNA repair enzymes that are DNA polymerases are also suitable and include DNA polymerase beta subunit (POLB); DNA polymerase gamma (POLG); DNA polymerase subunit delta (POLD1); DNA polymerase II subunit A (POLE); DNA polymerase delta auxiliary protein (PCNA); DNA polymerase zeta (POLZ); MAD2 homolog ((REV7); DNA polymerase eta (POLH): DNA polymerase kappa (POLK): and the like.

Various types of DNA repair enzymes that are often referred to as "editing and processing nucleases" include 3'-nuclease; 3'-exonuclease; 5'-exonuclease; endonuclease; and the like. Other examples of DNA repair enzymes include DNA helicases including such as ATP DNA helicase and so on. The DNA repair enzymes may be present as components of botanical extracts, bacterial lysates, biological materials, and the like. For example, botanical extracts may contain DNA repair enzymes.

Example 1

Sirt1 Activators (Orsirtine™ and Resveratrol) Improve Keratinocyte Survival Synergistically Orsirtine™ ((SEQ ID No. 8) G-L-Y-D-N-L-E) and resveratrol, mitosis delay agents, were tested for their ability to improve survival of UVB-irradiated human keratinocytes.
Methods:

Normal human keratinocytes were cultured in Epilife Medium with Human Keratinocyte Growth Supplement. The cells were sub-cultured into 96-well plates (Costar). Keratinocytes were pretreated with resveratrol (25 μM) and Orsirtine (1%, 3%) by themselves, and in a complex of resveratrol (25 μM) and Orsirtine™ (3%). Keratinocytes were treated with the undiluted complex and with dilutions of 1:2, 1:4 and 1:8 (complex: Epilife media).

Keratinocytes were incubated with these treatments overnight at 37° C.; 5% CO2. After 24 hours, the treatment was aspirated and keratinocytes were washed once in D-PBS. 100 μl of D-PBS was added for the irradiation. The cells were subjected to UVB irradiation at 0, 45, 90 and 135 mJ/cm$^2$ UVB. After the irradiation, D-PBS was removed. Keratinocytes were post treated appropriately and incubated overnight at 37° C.; 5% CO2. The next day, cells were assayed for viability, utilizing MTS reagent (CellTiter96, Promega). Absorbance readings were taken on the SpectraMax190 spectrophotometer (Molecular Devices) at 490 nm following an approximate two hour incubation at 37° C.; 5% CO2.
Results and Conclusion:

Referring to FIG. 2, at low UV irradiation (45 mJ/cm2) it has been documented that cells do not exhibit intense damage, so improvements in survivability were expected to be negligible. What we did observe however, is that cells treated with just resveratrol show a 20% decreased survival rate, and cells treated with just Orsitine™ 3%, show an 8% decreased survival rate. Nevertheless, cells treated with 1:2 diluted complex (resveratrol 25 μM and Orsirtine™ 3%) or with the undiluted complex tested the same as the control. Also, as the complex is diluted to 1:4 and then 1:8, survivability decreases. So resveratrol by itself, and Orsirtine 3% by itself, decrease cell survival. However, the combination of resveratrol and Orsirtine 3% does not decrease cell survival. But can the combination improve the rate of cell survival, over the control?

At 90 mJ/cm$^2$ UV irradiation, the survival rates of untreated cells was 47%. In comparison, survivability of cells treated with the undiluted and diluted complex (resveratrol 25 µM and Orsirtine™ 3%), followed a dose dependent relationship, as follows:

|  | Dilution of complex | | | |
|---|---|---|---|---|
|  | 1:8 | 1:4 | 1:2 | undiluted |
| Increased survival after 90 mJ/cm² UV | 28% | 34% | 60% | 64% | while survivability for cells treated with just Orsirtine™ or just resveratrol was as follows:

|  | Orsirtine ™ 3% | Orsirtine ™ 1% | Resveratrol 25 µM |
|---|---|---|---|
| Increased survival after 90 mJ/cm² UV | 11% | −17% | −15% |

At 135 mJ/cm² UV irradiation, the survival rate of untreated cells was 19%. In comparison, survivability for cells treated with the undiluted and diluted complex followed a quasi-dose dependent relationship, as follows:

|  | Dilution of complex | | | |
|---|---|---|---|---|
|  | 1:8 | 1:4 | 1:2 | undiluted |
| Increased survival after 135 mJ/cm² UV | 11% | 5% | 56% | 131% | while survivability for cells treated with just Orsirtine™ or just resveratrol was as follows:

|  | Orsirtine ™ 3% | Orsirtine ™ 1% | Resveratrol 25 µM |
|---|---|---|---|
| Increased survival after 135 mJ/cm² UV | 26% | 5% | 22% |

It can be concluded that the complex (resveratrol 25 µM and Orsirtine™ 3%) provided significant protection against UVB induced cytotoxicity and increased cell survival over the resveratrol and Orsirtine™ alone.

These numbers would also seem to suggest that the effect of the combination of Orsirtine™ and Resveratrol on keratinocyte survivability is synergistic. For example, 3% Orsirtine™, by itself, increases survivability by 11% (for UVB of 90 mJ/cm²) and by 26% (for UVB of 135 mJ/cm²). 25 µM Resveratrol, by itself, decreased survivability by 15% (for UVB of 90 mJ/cm²) and increased it by 22% (for UVB of 135 mJ/cm²). However, the undiluted combination 3% Orsirtine™ and 25 µM Resveratrol, increased keratinocyte survivability by an enormous and unexpected 64% (for UVB of 90 mJ/cm²) and 131% (for UVB of 135 mJ/cm²). Even when diluted down to 1:8, the combination still increases keratinocyte survivability by 28% (for UVB of 90 mJ/cm²) and 11% (for UVB of 135 mJ/cm²). This is wholly unexpected. Since Orsirtine™ is a known sirtuin activator and Resveratrol a suspected sirtuin activator, the tremendous improvement in keratinocyte survivability would not be expected by a person of ordinary skill in the art. At most, an additive effect might have been expected, but not a synergistic one.

What relative concentrations of (SEQ ID No. 8) G-L-Y-D-N-L-E and resveratrol will produce a substantial synergistic effect on keratinocyte survival? That question may be answered by routine experimentation, now that the effect has been identified. By "synergistic combination of sirt1 activator and resveratrol" we mean a combination of (SEQ ID No. 7) $(AA)_n$-G-L-Y-D-N-L-E-$(AA)_n$ and resveratrol or derivatives thereof, that increases the rate of keratinocyte survival (as such rates are measured by methods known in the art), by an amount that is more than the sum of the effect of each material individually.

Example 2

SIRT1 Activators, in the Right Concentrations Improve the Performance of Circadian Gene Activators and DNA Repair Enzymes Vis-À-Vis UVB Exposure According to methods described in Example 1, two complexes were tested at various dilutions, for their effect on keratinocyte survival, following UV exposure. Complex I consisted of Epilife Medium with Human Keratinocyte Growth Supplement and Chronolux (0.1%), *Bifidus* extract (12.4%), Adasome (0.05%) and Roxisome (0.05%). Complex II consisted of Complex I plus Orsirtine™ (0.08%) and Resveratrol (25 µM). Complex I was tested undiluted and at dilutions of 1:2 and 1:4 (complex:Epilife media). Complex II was tested undiluted and at dilutions of 1:2, 1:4 and 1:8. The media was used a as a control. Keratinocytes were exposed to UVB at levels of 100, 150 and 200 mL/cm².

Results and Conclusion:

Referring to FIG. 3, and comparing Complex II to Complex I within the same UVB exposure,

| Improvement: Complex II compared to Complex I | | | |
|---|---|---|---|
| Dilution of both complexes | 100 mJ/cm² | 150 mJ/cm² | 200 mJ/cm² |
| 1:4 | 10.2% | 4.7% | 3.8% |
| 1:2 | 3.2% | 7.2% | 9.6% |
| Undiluted | −5.7% | −3.0% | 3.6% |

In all cases but two, the Orsirtine™ and Resveratrol improve keratinocyte survival following UVB exposure compared to circadian gene activators alone. However, moving down the first two column (100 mJ/cm²), these data seem to suggest that the less sirt1 activator in combination with circadian gene activator, the better. However, that pattern is broken in columns 2 and 3 (150 mJ/cm² and 200 mJ/cm²), suggesting that an optimal combination of sirt1 and circadian gene activators depends on the amount of UVB to which the keratinocytes are exposed. In fact, moving across row 3 (undiluted) from left to right, the data suggests that the addition of Orsirtine™ and Resveratrol is warranted for greater amounts of UVB exposure. That pattern is also seen in the 1:2 dilution samples, but is reversed in the 1:4 dilution samples, suggesting that at lower UVB exposures, less sirt1 activation is needed. So, taken as a whole, the results of these experiments suggest that the optimal relative concentrations of circadian gene activators and sirt1 activators depends on the amount of UVB exposure. However, all Complex II test samples (circadian activator plus sirt1 activator) showed improvement in keratinocyte survivability over the controls. Determining optimal relative concentrations of circadian gene activators and sirt1 activators may require only routine experimentation, now that a person of ordinary skill in the art knows that that relative concentration is a results-effective variable, which was hitherto, unknown.

Compositions

The form of a composition of the present invention is not generally limited. For example, compositions of the invention may be in the form of emulsions, aqueous solutions or dispersions, gels, or anhydrous systems. If in the form of an emulsion, a composition may be a water in oil or oil in water emulsion. If in the form of an emulsion, the composition may contain from about 1-99%, preferably from about 5-90%, more preferably from about 10-85% water and from about 1-99%, preferably from about 5-90%, more preferably from about 5-75% of oil. If in the form of an aqueous suspension or dispersion, the composition may generally contain from about 1-99.9%, preferably from about 5-95%, more preferably from about 10-90% water, with the remaining ingredients being the active ingredients or other formula ingredients.

Preferably, the composition contains other ingredients that will provide a cosmetically or pharmaceutically acceptable product. Classes of such ingredients might include humectants, UVA and UVB sunscreens, surfactants, botanical extracts, biological materials, aqueous phase structuring agents (i.e. polysaccharides, acrylate polymers, high molecular weight PEG or polyglycerins), volatile and non-volatile oils (including silicones), vitamins, and antioxidants.

It is also possible that the circadian gene activators and the sirt1 activators are in separate compositions, that may be applied to the same area of skin in succession or that may be applied by dispensing an effective amount of each composition, mixing the compositions, and then applying the mixture to the skin.

Preferred Compositions

Preferred compositions are in the aqueous solution or emulsion form and contain at least one nonionic organic surfactant, at least one chemical sunscreen, at least one clock or per1 gene activator, at least one peptidic sirt1 activator, and at least one DNA repair enzyme. At least one botanical extract, and at least one oil may also be preferred.

More preferred is a composition where the nonionic organic surfactant is an alkoxylated alcohol, the chemical sunscreen is a UVB sunscreen, the clock or per1 keratinocyte gene activator is Tripeptide-32, the sirt1 activator is a combination Orsirtine™-like molecule and Resveratrol, the DNA repair enzyme is a mixture of *Arabidopsis Thaliana* extract, *Micrococcus* lysate, *Bifida* Ferment lysate, *Lactobacillus* ferment, and Plankton extract, and the at least one oil is an organic ester or hydrocarbon.

Methods of the Invention

The methods of the invention are primarily directed to repairing damage to human keratinocytes, preferably facial keratinocytes, which damage occurs in response to environmental aggressors. One method consists of applying to damaged human skin, a composition or compositions comprising at least one keratinocyte clock or per1 gene activator and at least one sirt1 activator. Optionally, the composition(s) of the method may comprise at least one DNA repair enzyme. By applying the composition after damage has occurred, the normal circadian cycle will be restored more quickly. However, the arrest of the cell cycle prior to mitosis will allow more time for DNA repair. By this method, substantial cellular damage will be reversed and/or will be checked from being passed on to daughter cells. The method will also improve keratinocyte viability and longevity.

The invention is also directed to a method of preventing or inhibiting damage to human keratinocytes, preferably facial keratinocytes, which damage would occur in response to environmental aggressors. The method consists of applying to human skin at risk of experiencing environmental damage, a composition or compositions comprising at least one keratinocyte clock or per1 gene activator and at least one sirt1 activator. Optionally, the composition(s) of the method may comprise at least one DNA repair enzyme. By applying the composition before damage has occurred, the normal circadian cycle may be more closely maintained and the normal cell cycle repair process may be more closely maintained. By this method, substantial cellular damage will be prevented and/or will be checked from being passed on to daughter cells. The method will also improve keratinocyte viability and longevity.

In the methods of the invention, the composition(s) may be applied to skin one or more times per day. For example, the composition(s) may be applied to skin in the morning prior to beginning daily activities and/or at night, immediately prior to retiring. These times are preferred, because the skin is generally under the least amount of environmental assault, meaning that skin cell repair may be maximized. At these times. "Immediately prior to retiring" or "immediately prior to nightly rest" mean within one hour of going to bed, more preferably, within 30 minutes of going to bed. In the morning is more of a preventive approach, while immediately before retiring, or in the evening are more of a repair approach. The composition(s) may be applied as part of a regimen; that is, the skin is cleansed and treated with toner, after which the composition(s) of the invention are applied. The composition(s) may be part of a kit that contains a cleanser, a toner, and the composition(s) of the invention.

Preferably the composition(s) are applied to the skin of the face and/or neck and décolletage immediately prior to retiring, to repair DNA damaged keratinocytes and provide general improvement of the skin. Combining the clock and per1 gene activators with sirt1 activators (and preferably, DNA repair enzymes) in a composition used to treat facial skin at night, immediately prior to retiring, maximizes the keratinocyte repair of DNA damage, and also promotes cellular viability, longevity, and health.

As noted above, it is also possible that the circadian gene activators and the sirt1 activators are in separate compositions. In that case, methods of the invention include steps of applying each composition to the same area of skin in succession or dispensing an effective amount of each composition, mixing the compositions, and then applying the mixture to the skin.

EXAMPLES

The invention will be further described in connection with the following examples which are set forth for the purposes of illustration only. Skin treatment compositions may be prepared as follows.

Example 1

| Ingredient | w/w % | w/w % |
|---|---|---|
| Oleth-3 phosphate | 0.45 | 0.45 |
| Oleth-3 | 0.35 | 0.35 |
| Oleth-5 | 0.24 | 0.24 |
| Butylene glycol | 0.20 | 0.20 |
| Squalane | 0.50 | 0.50 |
| BHT | 0.10 | 0.10 |
| Ethylhexyl methoxycinnamate | 0.10 | 0.10 |
| Choleth-24/ceteth-24 | 0.10 | 0.10 |
| Triethanolamine | 0.11 | 0.11 |
| Retinyl palmitate/*zea mays* (corn) oil/BHT/BHA | 0.10 | 0.10 |
| Butylene glycol | 1.10 | 1.10 |
| Chamomile | 0.03 | 0.03 |
| Bisabolol | 0.10 | 0.10 |
| Methyl paraben | 0.46 | 0.46 |
| PEG-75 | 4.00 | 4.00 |
| Bis-PEG-18 methyl ether dimethyl silane | 2.00 | 2.00 |
| Glycereth-26 | 1.00 | 1.00 |
| Methyl gluceth-20 | 4.00 | 4.00 |
| Trisodium EDTA | 0.10 | 0.10 |
| Pantethine | 0.14 | 0.14 |
| Caffeine | 0.05 | 0.05 |
| Xanthan gum | 0.075 | 0.075 |
| Carbomer | 0.26 | 0.26 |
| Triethanolamine | 0.50 | 0.50 |
| Phenoxyethanol | 0.70 | 0.70 |
| Benzyl alcohol | 0.10 | 0.10 |
| Bifida ferment lysate | 9.40 | 9.40 |
| Water/bifida ferment lysate/hydrogenated lecithin | 3.00 | 3.00 |
| Butylene glycol/water/*Cola Acuminata* extract | 3.00 | 3.00 |
| Sodium ribonucleic acid | 0.01 | 0.01 |
| Water/butylene glycol/tripeptide-32 | 0.10 | 0.10 |
| *Lactobacillus* ferment/lecithin/water | 0.05 | 0.05 |
| Water/*Arabidopsis Thaliana* extract/lecithin | 0.05 | 0.05 |
| Orsirtine 10x | 0.08 | 0.08 |
| Resveratrol | — | 25 μM |
| Phenoxyethanol | 0.02 | 0.02 |
| Sodium hyaluronate | 0.01 | 0.01 |
| FD&C Red No. 4 (1% aqueous solution with butylene glycol) | 0.04 | 0.04 |
| FD&C Yellow No. 5 (1% aqueous solution with butylene glycol) | 0.09 | 0.09 |
| D&C Green No. 5 (0.1% solution with butylene glycol) | 0.001 | 0.001 |
| Water | QS | QS |

Examples 2-4

Composition A (example 2) comprises circadian gene activators, and sirt1 activators, Orsirtine™ and resveratrol. Thus composition A is intended for use by itself. Composition B (example 3) comprises Chronolux® (circadian gene activator), but no sirt1 gene activators. Thus composition B is intended for use with a separate composition having sirt1 gene activating ability, such as composition C (example 4). The compositions are prepared by combining the ingredients and mixing well to form a liquid. The compositions may be stored in brown glass bottles.

| Ingredient | A (w/w %) | B (w/w %) |
|---|---|---|
| Oleth-3 phosphate | 0.45 | 0.45 |
| Oleth-3 | 0.35 | 0.35 |
| Oleth-5 | 0.24 | 0.24 |
| Butylene glycol | 0.20 | 0.20 |
| Squalane | 0.50 | 0.50 |
| BHT | 0.10 | 0.10 |
| Ethylhexyl methoxycinnamate | 0.10 | 0.10 |
| Choleth-24/ceteth-24 | 0.10 | 0.10 |
| Triethanolamine | 0.11 | 0.11 |
| Retinyl palmitate/*zea mays* (corn) oil/BHT/BHA | 0.10 | 0.10 |
| Butylene glycol | 1.10 | 1.10 |
| Chamomile | 0.03 | 0.03 |
| Bisabolol | 0.10 | 0.10 |
| Water | QS | QS |
| Methyl paraben | 0.46 | 0.46 |
| PEG-75 | 4.00 | 4.00 |
| Bis-PEG-18 methyl ether dimethyl silane | 2.00 | 2.00 |
| Glycereth-26 | 1.00 | 1.00 |
| Methyl gluceth-20 | 4.00 | 4.00 |
| Trisodium EDTA | 0.10 | 0.10 |
| Pantethine | 0.14 | 0.14 |
| Caffeine | 0.05 | 0.05 |
| Xanthan gum | 0.075 | 0.075 |
| Carbomer | 0.26 | 0.26 |
| Triethanolamine | 0.50 | 0.50 |
| Phenoxyethanol | 0.70 | 0.70 |
| Benzyl alcohol | 0.10 | 0.10 |
| Bifida ferment lysate | 9.40 | 9.40 |
| Water/bifida ferment lysate/hydrogenated lecithin | 3.00 | 3.00 |
| Butylene glycol/water/*Cola Acuminata* extract | 3.00 | 3.00 |
| Sodium ribonucleic acid | 0.01 | 0.01 |
| Water/butylene glycol/tripeptide-32 (Chronolux ®) | 0.20 | 0.20 |
| Water/butylene glycol/hydrolyzed rice extract (Orsirtine ™) | 0.08 | — |
| Resveratrol | 25 μM | — |
| *Lactobacillus* ferment/lecithin/water | 0.05 | 0.05 |
| Water/*Arabidopsis Thaliana* extract/lecithin | 0.05 | 0.05 |
| Phenoxyethanol | 0.02 | 0.02 |
| Sodium hyaluronate | 0.01 | 0.01 |
| FD&C Red No. 4 (1% aqueous solution with butylene glycol) | 0.04 | 0.04 |
| FD&C Yellow No. 5 (1% aqueous solution with butylene glycol) | 0.09 | 0.09 |
| D&C Green No. 5 (0.1% solution with butylene glycol) | 0.001 | 0.001 |

| Ingredient | C (w/w %) |
|---|---|
| CREATINE | 0.08 |
| TREHALOSE | 0.50 |
| ACETYL GLUCOSAMINE | 0.50 |
| CAFFEINE | 0.20 |
| CARBOMER | 0.15 |
| ACRYLATES/C10-30 ALKYL ACRYLATE CROSSPOLYMER/PHENOXYETHANOL | 0.108 |
| AMMONIUM ACRYLOYLDIMETHYLTAURATE/VP COPOLYMER | 0.50 |
| BUTYLENE GLYCOL | 1.00 |
| XANTHAN GUM | 0.08 |
| SODIUM HYDROXIDE | 0.03 |
| CETYL ALCOHOL | 2.00 |
| C12-20 ACID PEG-8 ESTER | 3.00 |
| CAPRYLIC/CAPRIC TRIGLYCERIDE | 5.90 |
| DIMETHICONE | 0.50 |
| POTASSIUM CETYL PHOSPHATE | 0.20 |
| *COCOS NUCIFERA* (COCONUT) OIL/*ALOE BARBADENSIS* LEAF EXTRACT | 1.60 |
| CHOLESTEROL/POTASSIUM SULFATE | 0.05 |
| PEG-100 STEARATE | 0.75 |
| PHYTANTRIOL | 0.50 |
| *TRITICUM VULGARE* (WHEAT BRAN) EXTRACT/*OLEA EUROPAEA* (OLIVE) FRUIT EXTRACT | 0.20 |
| *PUNICA GRANATUM* (POMEGRANATE) STEROLS | 0.50 |
| PENTYLENE GLYCOL | 1.00 |
| PHENOXYETHANOL | 0.30 |

| | |
|---|---|
| GLYCERINE USP99% (vegetable) | 2.00 |
| ETHYLHEXYLGLYCERIN | 1.00 |
| YEAST FERMENT EXTRACT (*POLYGONUM CUSPIDATUM* ROOT EXTRACT (resveratrol)/ *HUMULUS LUPULUS* EXTRACT/ LINOLEIC ACID/LINOLENIC ACID/*VITIS VINIFERA* SEED EXTRACT/*ROSMARINUS OFFICINALIS* EXTRACT/ *SELAGINELLA TAMARISCINA* EXTRACT/ CYCLODEXTRIN/ETHYLBISIMINOMETHYLGUAIACOL MANGANESE CHLORIDE/*CITRUS RETICULATA* PEEL EXTRACT/*PUNICA GRANATUM* JUICE EXTRACT/NORDIHYDROGUAIARETIC ACID/SIMETHICONE) | 0.50 |
| *LARIX SIBIRICA* WOOD EXTRACT | 0.10 |
| *LAMINARIA SACCHARINA* EXTRACT | 0.50 |
| YEAST EXTRACT SOLUTION (ADENOSINE PHOSPHATE/PHENOXYETHANOL/SIMETHICONE | 0.50 |
| ACETYL HEXAPEPTIDE-8 | 0.50 |
| SODIUM PCA | 0.50 |
| *SIGESBECKIA ORIENTALIS* (ST. PAUL'S WORT) EXTRACT | 0.50 |
| GLYCERIN/*PADINA PAVONICA THALLUS* EXTRACT | 0.10 |
| *ARGANIA SPINOSA* LEAF EXTRACT | 0.10 |
| WATER/BUTYLENE GLYCOL/*TAMARINDUS INDICA* SEED EXTRACT | 0.10 |
| PROPYLENE GLYCOL DICAPRATE/*HELIANTHUS ANNUUS* (SUNFLOWER) SEEDCAKE/ *HORDEUM VULGARE* (BARLEY) EXTRACT/ *CUCUMIS SATIVUS* (CUCUMBER) FRUIT EXTRACT | 0.50 |
| BUTYLENE GLYCOL/*CENTAURIUM ERYTHRAEA* (CENTAURY) EXTRACT | 0.50 |
| Water/butylene glycol/hydrolyzed rice extract (Orsirtine ™) | 0.08 |
| SODIUM HYALURONATE | 2.50 |
| HYALURONIC ACID | 0.02 |
| FRAGRANCE (PARFUM) | 0.125 |
| SODIUM ACRYLATE/SODIUM ACRYLOYLDIMETHYL TAURATE COPOLYMER/HYDROGENATED POLYDECENE/LAURETH-8 | 0.001 |
| WATER | Q.S. |

While the invention has been described in connection with the preferred embodiment, it is not intended to limit the scope of the invention to a particular form set forth. On the contrary, this description is intended to cover such alternatives, modifications, and equivalents as may be included within the spirit and scope of the invention, as defined by the appended claims.

We claim:

1. A skin care composition comprising tripeptide-32 and a synergistic combination of resveratrol and the peptide (SEQ ID No. 8)
    G-L-Y-D-N-L-E Gly-Leu-Tyr-Asp-Asn-Leu-Glu.

2. A skin care composition comprising:
    tripeptide-32, between 0.00001 and 25%, with respect to the total weight of the final composition;
    (SEQ ID No. 8) G-L-Y-D-N-L-E, between 0.0001% and 5%, with respect to the total weight of the final composition; and
    resveratrol, between 0.001% to about 95%, with respect to the total weight of the final composition.

3. The composition according to claim 2 further comprising at least one DNA repair enzyme between 0.0001% and 25%, with respect to the total weight of the final composition.

4. The composition of claim 3 wherein the DNA repair enzyme is selected from the group consisting of base excision repair (BER) enzymes, nucleotide excision repair (NER) enzymes, DNA polymerases, DNA helicases, mismatch repair (MMR) enzymes, and mixtures thereof.

5. The composition of claim 3 wherein the DNA repair enzyme is selected from the group consisting of *Arabidopsis Thaliana* extract, *Lactobacillus* ferment, *Micrococcus* lysate, Plankton extract, *Bifida* ferment lysate, and mixtures thereof.

6. A method of inhibiting damage to human keratinocytes due to environmental aggressors comprising:
    applying to skin at risk of keratinocyte damage, the composition of claim 1.

7. The method of claim 6 wherein the composition is part of a single composition that is chemically, thermodynamically and light stable.

8. A method of repairing damage to human keratinocytes due to environmental aggressors comprising:
    applying to the face, the composition of claim 1.

9. The method of claim 8 wherein the composition is applied within 30 minutes of going to bed.

10. The method of claim 8 comprising:
    cleansing a portion of human skin;
    then applying a toner to the portion of skin; and
    then applying the composition.

11. The method according to claim 8 wherein the environmental aggressor is UVB radiation.

12. The method according to claim 8 wherein the damage to human keratinocytes is UVB damage to human keratinocytes.

13. The composition of claim 1 further comprising:
    at least one aqueous phase structuring agent comprising a polysaccharide, an acrylic polymer, or mixtures thereof;
    at least one nonionic organic surfactant which is an alkoxylated alcohol; and
    at least one humectant which is a C2-4 alkylene glycol or glycerin.

* * * * *